(12) United States Patent
Vandenbroeck et al.

(10) Patent No.: US 8,846,345 B2
(45) Date of Patent: Sep. 30, 2014

(54) RECOMBINANT CELL LINE

(75) Inventors: Koen Vandenbroeck, Bangor (GB); Iraide Alloza, Bangor (GB)

(73) Assignee: The Queen's University of Belfast, Belfast (GB)

( * ) Notice: Subject to any disclaimer, the term of this patent is extended or adjusted under 35 U.S.C. 154(b) by 2346 days.

(21) Appl. No.: 10/537,647

(22) PCT Filed: Dec. 8, 2003

(86) PCT No.: PCT/IB03/06404
§ 371 (c)(1),
(2), (4) Date: Dec. 28, 2005

(87) PCT Pub. No.: WO2004/052929
PCT Pub. Date: Jun. 24, 2004

(65) Prior Publication Data
US 2006/0160147 A1    Jul. 20, 2006

(30) Foreign Application Priority Data
Dec. 6, 2002   (GB) .................................. 0228465.1

(51) Int. Cl.
*C12N 15/09* (2006.01)
*C12N 5/00* (2006.01)

(52) U.S. Cl.
USPC ...................................... 435/69.52; 435/325

(58) Field of Classification Search
None
See application file for complete search history.

(56) References Cited

U.S. PATENT DOCUMENTS 5,972,986 A * 10/1999 Seibert et al. ................. 514/406
6,630,324 B1 * 10/2003 Barski et al. ................. 435/69.1
2002/0119193 A1   8/2002 Le et al. ........................ 424/465

OTHER PUBLICATIONS

Dunlop et al., "Inducible Expression and Pharmacology of the Human Excitatory Amino Acid Transporter 2 Subtype of L-Glutamate Transporter", *British Journal of Pharmacology* 128:1485-1490 (1999).
Graham et al., "Ecdysone-Controlled Expression of Transgenes", *Expert Opinion on Biological Therapy* 2:525-535 (2002).
Martens et al., "Protein Disulfide Isomerase-Mediated Cell-Free Assembly of Recombinant Interleukin-12 p40 Homodimers", *European Journal of Biochemistry* 267:6679-6683 (2000).
Nagy et al., "Inducible Expression and Pharmacology of Recombinant NMDA Receptors, Composed of Rat NR1a/NR2B Subunits", *Neurochemistry International* 43:19-29 (2003).
Davies et al., "Clinical Pharmacokinetics and Pharmacodynamics of Celecoxib", *Clinical Pharmacokinetics* 38:225-242 (2000).
Chen et al., "Selective Inhibition of COX-2 Is Beneficial to Mice Infected Intranasally With VSV" *Prostaglandins and Other Lipid Mediators* 67:143-155 (2002).
Cuzzocrea et al., "Celecoxib, A Selective Cyclo-Oxygenase-2 Inhibitor Reduces the Severity of Experimental Colitis Induced by Dinitrobenze Sulfonic Acid in Rats", *European Journal Pharmacology* 431:91-102 (2001).

* cited by examiner

*Primary Examiner* — Catherine Hibbert
(74) *Attorney, Agent, or Firm* — Drinker Biddle & Reath LLP

(57) ABSTRACT

The invention relates to a recombinant cell line capable of inducible expression of an α and/or β subunit of interleukin 12 (IL-12), and an ecdosyme-inducible expression vector capable of transfecting a host cell to produce the recombinant cell line of the invention. The invention also relates to a method of screening a candidate compound for the ability to inhibit IL-12 formation and secretion which comprises the steps of incubating a cell line according to the invention with the candidate compound and then assaying the cell line culture for secreted IL-12, or a subunit thereof.

10 Claims, 10 Drawing Sheets

A  Nhel restriction site
5' CAG [GCT AGC] GCA GCC ATG TGT CCA GCG CGC AGC 3'

B  5' CTG [CTC GAG] TTA ATG GTG ATG GTG ATG GTG GGA AGC ATT CAG ATA GCT 3'
   Xhol restriction site C  Nhel restriction site
5' CAG [GCT AGC] GCA GCC ATG TGT CAC CAG CAG TTG 3'

D  5' CTG [CTC GAG] CTA ATG GTG ATG GTG ATG GTG ACT GCA GGG CAC AGA TG 3'
   Xhol restriction site E  5' CTG [CTC GAG] CTA ACT GCA GGG CAC AGA TG 3'
   Xhol restriction site

Fig. 3.

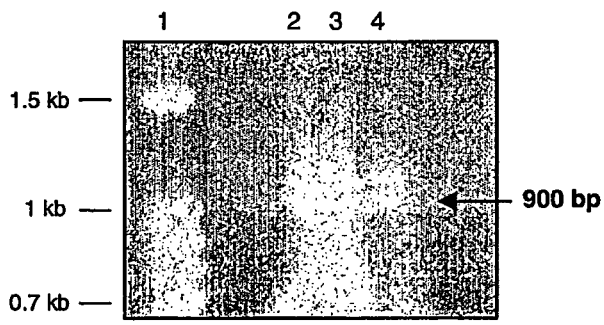

Fig. 4.

SEQUENCE LISTING

```
<160> NUMBER OF SEQ ID NOS: 8

<210> SEQ ID NO 1
<211> LENGTH: 33
<212> TYPE: DNA
<213> ORGANISM: Artificial
<220> FEATURE:
<223> OTHER INFORMATION: IL-12 alpha chain forward primer

<400> SEQUENCE: 1
caggctagcg cagccatgtg tccagcgcgc agc                                33

<210> SEQ ID NO 2
<211> LENGTH: 48
<212> TYPE: DNA
<213> ORGANISM: Artificial
<220> FEATURE:
<223> OTHER INFORMATION: IL-12 alpha chain reverse primer with 6His tag

<400> SEQUENCE: 2
ctgctcgagt taatggtgat ggtgatggtg ggaagcattc agatagct                 48

<210> SEQ ID NO 3
<211> LENGTH: 34
<212> TYPE: DNA
<213> ORGANISM: Artificial
<220> FEATURE:
<223> OTHER INFORMATION: IL-12 beta chain forward primer

<400> SEQUENCE: 3
caggctagcg cagccatggt gtcaccagca gttg                               34

<210> SEQ ID NO 4
<211> LENGTH: 47
<212> TYPE: DNA
<213> ORGANISM: Artificial
<220> FEATURE:
```

<223> OTHER INFORMATION: IL-12 beta chain reverse primer with 6His tag

<400> SEQUENCE: 4
ctgctcgagc taatggtgat ggtgatggtg actgcagggc acagatg    47

<210> SEQ ID NO 5
<211> LENGTH: 29
<212> TYPE: DNA
<213> ORGANISM: Artificial
<220> FEATURE:
<223> OTHER INFORMATION: IL-12 beta chain reverse primer without 6His
      tag

<400> SEQUENCE: 5
ctgctcgagc taactgcagg gcacagatg    29

<210> SEQ ID NO 6
<211> LENGTH: 702
<212> TYPE: DNA
<213> ORGANISM: Artificial
<220> FEATURE:
<223> OTHER INFORMATION: cDNA for alpha chain of IL-12

<400> SEQUENCE: 6
caggctagcg cagccatgtg tccagcgcgc agcctcctcc ttgtggctac cctggtcctc    60
ctggaccacc tcagtttggc cagaaacctc cccgtggcca ctccagaccc aggaatgttc    120
ccatgccttc accactccca aacctgctg agggccgtca gcaacatgct ccagaaggcc    180
agacaaactc tagaatttta cccttgcact tctgaagaga ttgatcatga agatatcaca    240
aaagataaaa ccagcacagt ggaggcctgt ttaccattgg aattaaccaa gaatgagagt    300
tgcctaaatt ccagagagac tctttcata actaatggga gttgcctggc tccagaaaag    360
acctctttta tgatggccct gtgccttagt agtatttatg aagacttgaa gatgtaccag    420
gtggagttca agaccatgaa tgcaaagctt ctgatggatc ctaagaggca gatctttcta    480
gatcaaaaca tgctggcagt tattgatgag ctgatgcagg ccctgaattt caacagtgag    540
actgtgccac aaaaatcctc ccttgaagaa ccggattttt ataaaactaa aatcaagctc    600
tgcatacttc ttcatgcttt cagaattcgg gcagtgacta ttgacagagt gacgagctat    660
ctgaatgctt cccaccatca ccatcaccat taactcgagc ag    702

<210> SEQ ID NO 7
<211> LENGTH: 1029
<212> TYPE: DNA
<213> ORGANISM: Artificial
<220> FEATURE:
<223> OTHER INFORMATION: cDNA for beta chain of IL-12

<400> SEQUENCE: 7
caggctagcg cagccatgtg tcaccagcag ttggtcatct cttggttttc cctggttttt    60
ctggcatctc ccctcgtggc catatgggaa ctgaagaaag atgtttatgt cgtagaattg    120
gattggtatc cggatgcccc tggagaaatg gtggtcctca cctgtgacac ccctgaagaa    180
gatggtatca cctggacctt ggaccagagc agtgaggtct taggctctgg caaaaccctg    240
accatccaag tcaaagagtt tggagatgct ggccagtaca cctgtcacaa ggaggcgag    300
gttctaagcc attcgctcct gctgcttcac aaaaaggaag atggaatttg gtccactgat    360
atttaaagg accagaaaga acccaaaaat aagacctttc taagatgcga ggccaagaat    420
tattctggac gtttcacctg ctggtggctg acgacaatca gtactgattt gacattcagt    480

```
gtcaaaagca gcagaggctc ttctgacccc caagggggtga cgtgcggagc tgctacactc    540
tctgcagaga gagtcagagg ggacaacaag gagtatgagt actcagtgga gtgccaggag    600
gacagtgcct gcccagctgc tgaggagagt ctgcccattg aggtcatggt ggatgccgtt    660
cacaagctca agtatgaaaa ctacaccagc agcttcttca tcagggacat catcaaacct    720
gacccaccca agaacttgca gctgaagcca ttaaagaatt ctcggcaggt ggaggtcagc    780
tgggagtacc ctgacacctg gagtactcca cattcctact tctccctgac attctgcgtt    840
caggtccagg gcaagagcaa gagagaaaag aaagatagag tcttcacgga caagacctca    900
gccacggtca tctgccgcaa aaatgccagc attagcgtgc gggcccagga ccgctactat    960
agctcatctt ggagcgaatg ggcatctgtg ccctgcagtc accatcacca tcaccattag   1020
ctcgagcag                                                            1029

<210> SEQ ID NO 8
<211> LENGTH: 612
<212> TYPE: DNA
<213> ORGANISM: Artificial
<220> FEATURE:
<223> OTHER INFORMATION: cDNA for p19 chain of IL-23

<400> SEQUENCE: 8
caggctagcg cagccatgct ggggagcaga gctgtaatgc tgctgttgct gctgccctgg     60
acagctcagg gcagagctgt gcctggggggc agcagccctg cctggactca gtgccagcag   120
ctttcacaga agctctgcac actggcctgg agtgcacatc cactagtggg acacatggat   180
ctaagagaag agggagatga agagactaca aatgatgttc cccatatcca gtgtggagat   240
ggctgtgacc cccaaggact cagggacaac agtcagttct gcttgcaaag gatccaccag   300
ggtctgattt tttatgagaa gctgctagga tcggatattt tcacagggga gccttctctg   360
ctccctgata gccctgtggg ccagcttcat gcctccctac tgggcctcag ccaactcctg   420
cagcctgagg gtcaccactg ggagactcag cagattccaa gcctcagtcc cagccagcca   480
tggcagcgtc tccttctccg cttcaaaatc cttcgcagcc tccaggcctt tgtggctgta   540
gccgcccggg tctttgccca tggagcagca accctgagtc cccaccatca ccatcaccat   600
taactcgagc ag                                                        612
```

RECOMBINANT CELL LINE

The invention also relates to recombinant cell lines transformed to express a dimeric form of interleukin, or a subunit thereof, and expression vectors used to transform the cell lines. The invention also relates to a method of screening candidate compounds for the ability to inhibit assembly and secretion of dimeric forms of interleukins, or subunits thereof.

BACKGROUND ART

Cytokines are a unique family of growth factors. Secreted primarily from leukocytes, cytokines stimulate both the humoral and cellular immune responses, as well as the activation of phagocytic cells. Cytokines secreted from lymphocytes are termed lymphokines, whereas those secreted by monocytes or macrophages are termed monokines. Many of the lymphokines are also known as interleukins (IL's), since they are not only secreted by leukocytes, but are also able to affect the cellular responses of leukocytes. Specifically, interleukins are growth factors targeted to cells of hematopoietic origin. One of the interleukins, IL-12, is a pro-inflammatory cytokine interleukin. This cytokine is predominantly secreted either as a αβ heterodimeric form or as a ββ homodimeric form. Both dimer forms bind the IL-12-receptor on target cells but differ in the spectrum of biological activities induced. The αβ form is crucial for generation of cell-mediated immunity against parasites, viruses and bacteria, but contributes also to destructive effects in pathogenesis of autoimmune diseases, e.g. MS, RA and inflammatory bowel disease. The ββ form has been shown to be instrumental in virus-induced inflammation, and in excessive epithelial airway inflammation seen in asthma. Thus, both forms of IL-12 are disease-promoting factors in a variety of conditions. Recently, two novel cytokines have been discovered, named interleukin-23 and interleukin-27 that apparantly belong to the IL-12 subclass of cytokines based on structural relationships. Both IL-23 and IL-27 share with IL-12 a typical heterodimeric structure and are invloved in a similar array of immune responses.

Celebrex is a diaryl-substituted pyrazole. It is a nonsteroidal anti-inflammatory drug (NSAID) that is indicated for the treatment of osteoarthritis, rheumatoid arthritis, for the management of acute pain in adults for the treatment of primary dysmenorrhea. The mechanism of action of CELEBREX is believed to be due to inhibition of prostaglandin synthesis, primarily via inhibition of cyclooxgenase-2 (COX-2). Scientific literature indicates that CELEBREX displays antitumor effects by sensitizing cancer cells to apoptosis. A recent paper has indicated that CELEBREX blocks the endoplasmic reticulum (ER) $Ca^{2+}$-ATPases, and it has been suggested that this $Ca^{2+}$ perturbation may be part of the signaling mechanism by which CELEBREX triggers apoptosis. This $Ca^{2+}$ perturbation effect seems to be unique to CELEBREX and was not seen with any of the other COX inhibitors (e.g. aspirin, ibuprofen, naproxen etc.)

STATEMENT OF INVENTION

According to the invention, there is provided an expression vector comprising DNA encoding a subunit of a dimeric form of interleukin under transcriptional control of an ecdysone-inducible promoter.

Suitably, the subunit of a dimeric form of interleukin is selected from the group comprising: p35 (alpha) subunit of interleukin 12 (IL-12); p40 (beta) subunit of IL-12; p19 chain of IL-23; p40 subunit of IL-23; ebi3 subunit of IL-27; and p28 subunit of Il-27.

Typically, the vector comprises an ecdysone-inducible mammalian expression plasmid, wherein the DNA encoding the subunit of a dimeric form of interleukin is included in the plasmid.

In one embodiment of the invention, the vector comprises DNA encoding a p40 subunit of IL-12. Cell lines stably transfected with such a vector will, when induced, express both homodimeric IL-12 and the beta-subunit of IL-12.

In another embodiment of the invention, the vector comprises DNA encoding a p35 subunit of IL-12. Cell lines stably transfected with such a vector will, when induced, express the alpha-subunit of IL-12.

In another embodiment of the invention, the vector comprises DNA encoding a p19 subunit of IL-23. Cell lines stably transfected with such a vector will, when induced, express the p19 subunit of IL-23.

In a preferred embodiment of the invention, the ecdysone inducible mammalian expression vector is selected from the group comprising: pIND; pIND(SP1); and pINDHygro.

In a particularly preferred embodiment of the invention, the DNA encoding a subunit of dimeric interleukin 12 includes a DNA sequence encoding a 6× histidine tag.

In one embodiment of the invention, the expression vector is selected from the group comprising: pIND-p35H; pIND (SP1)-p35H; pIND-40H; pINDHygro-p40; pIND(SP1)-p40H; and pIND-p40.

Suitably, the DNA encoding the subunit of dimeric interleukin is digested with NheI and XhoI restriction enzymes prior to ligation of the digested DNA products into the expression vector.

The invention also relates to an expression vector pIND (SP1)-p35H having ECACC accession number 03120401. A sample of this vector was deposited at the ECACC on 4 Dec. 2003.

The invention also relates to a method a producing a tightly controlled expression vector capable of transforming a host cell which when transformed is capable of producing a recombinant dimeric interleukin, or a subunit thereof, under transcriptional control of a ecdosone inducible promoter, comprising the steps of:
  providing cDNA for a subunits of a dimeric interleukin;
  digesting the cDNA with at least one restriction enzyme; and
  ligating the digested cDNA product into an ecdysone-inducible mammalian expression vector.

In a preferred embodiment of the invention, the DNA is digested with two restriction enzymes, these being NheI and XhoI. Suitably, the plasmid into which the digested DNA is to be ligated is also digested with the same restriction enzymes.

The invention also relates to an expression vector obtainable by the method of the invention.

The invention also relates to a cell line transfected with at least one expression vector of the invention, wherein the DNA encoding the at least one subunit of a dimeric interleukin is under transcriptional control of a ecdysone-inducible mammalian expression system.

Suitably, the ecdysone-inducible mammalian expression system comprises a plasmid other the expression vector of the invention which constitutively expresses two receptors which interact in the presence of ecdysone, or an analog thereof, to form a complex which binds to a response element of a promotor controlling DNA encoding the at least one subunit of a dimeric interleukin. Such a plasmid is sold by Invitrogen under the name pVgRxR.

In one embodiment, the cell line is transfected with DNA that encodes a p35 (beta) subunit of IL-12. Such a cell line, when induced, produces homodimeric IL-12 and the beta-subunit of IL-12.

In another embodiment, the cell line is transfected with an expression vector which includes DNA encoding the p40 subunit of IL-12, and a further expression vector which includes DNA encoding the p35 subunit of IL-12. Such a cell line, when induced, produces heterodimeric IL-12.

In another embodiment, the cell line is transfected with an expression vector which includes DNA encoding the p40 subunit of IL-12 (which is identical to the p40 subunit of IL-23), and a further expression vector which includes DNA encoding the p19 subunit of IL-23. Such a cell line, when induced, produces heterodimeric IL-23.

Typically, the cell lines of the invention include the plasmid pVgRxR.

In one embodiment of the invention, the cells of the cell line are human embryonic kidney cells, preferably EcR293 cells.

The invention also relates to a cell line according to the invention in which the cells are natural beta-subunit-producing cells such as a HIBERNIAL cell line.

The invention also relates to a cell line having ECACC accession number 03112701. This cell line includes an expression vector having DNA encoding for the p40 (beta) subunit of IL-12. A deposit of the recombinant cells was made at the ECACC on 27 Nov. 2003.

The invention also relates to a method of producing a cell line capable of producing a recombinant dimeric interleukin, or a subunit thereof, under transcriptional control of a ecdysone-inducible promoter, comprising the steps of:
  providing at least one expression vector according to the invention; and
  transfecting a host cell with the at least one expression vector,
    wherein the DNA encoding the at least one subunit of a dimeric interleukin is under the transcriptional control of a ecdysone-inducible mammalian expression system.

The invention also relates to a method of preparing cDNA encoding a subunit of a dimeric form of interleukin comprising the steps of providing cDNA encoding the subunit, and digesting the cDNA with restriction enzymes NheI and XhoI to obtain a cDNA product.

The invention also relates to a method of screening a candidate compound for the ability to inhibit dimer assembly and secretion of a dimeric form of interleukin, comprising the steps of:
  incubating a cell culture comprising a cell line of the invention with the candidate compound;
  inducing transcription of the dimeric interleukin in the cells of the culture using ecdysone or an ecdysone analog; and
  assaying the cell culture for the presence of secreted interleukin.

In one embodiment of the method, the interleukin expressed by the cell line has a 6× histidine amino acid sequence tagged on either or both of the subunits thereof, wherein the assaying step involves Ni-NTA affinity chromatography.

Alternatively, the assaying step involves probing the cell culture with an antibody specific to a dimeric form of interleukin, or a subunit thereof.

The invention also relates to an inhibitor of dimer assembly and secretion of dimeric interleukin identified by the method of the invention.

The invention also relates to a method of prevention or treatment of inflammatory disease comprising a step of treating an individual with an inhibitor identified by the method of the invention. One such inhibitor IDENTIFIED is CELEBREX.

In a further aspect, the invention provides a method of treating disease having a pathogenesis which includes endogenous production of any of cytokines IL-12, IL 23 or IL-27, the method comprising a step of treating an individual with an endoplasmic reticulum (ER) $Ca^{2+}$ perturbation reagent.

In a further aspect, the invention provides the use of an ER $Ca^{2+}$ perturbation reagent in the manufacture of a medicament for the treatment of disease having a pathogenesis which includes endogenous production of any of cytokines IL-12, IL-23 or IL-27.

In a further aspect, the invention provides the use of an ER $Ca^{2+}$ perturbation reagent for the treatment of disease having a pathogenesis which includes endogenous production of any of cytokines IL-12, IL-23 or IL-27.

In a further aspect, the invention relates to a method of inhibiting the formation of one or more cytokines in an individual, which method comprises the step of treating an individual with ER $Ca^{2+}$ perturbation reagent. In one embodiment, the cytokines are selected from IL-12, IL-23 and IL-27.

In a further aspect, the invention relates to the use of an ER $Ca^{2+}$ perturbation reagent to inhibit the formation of one or more cytokines in an individual. In one embodiment the cytokines are selected from IL-12, IL-23 and IL-27.

In a preferred embodiment, the disease is an inflammatory disease. More preferably, the disease is a disease in which one or more endogenously produced IL-12 forms play a disease promoting role. Typically, the IL-12 forms are $\alpha\beta$ heterodimeric and $\beta\beta$ homodimeric forms.

In one embodiment, diseases in which cyclooxygenase-2 (COX-2) is reported to play a substantial disease promoting role are disclaimed.

In one embodiment, the inflammatory disease is a disease in which the endogenous production of one or both of $\alpha\beta$ and $\beta\beta$ forms of IL-12 is known to lead to disease in a COX-2 independent manner.

The invention also relates to a method of inhibiting the production of one or more cytokines in an individual in a post-translational manner, which method comprises a step of treating an individual with ER $Ca^{2+}$ perturbation reagent.

Preferably, the disease is selected from the group consisting of infectious diseases; bacterial protozoal or virus-induced inflammation; epithelial airway inflammation such as asthma; allergic disease; autoimmune disease such as MS, RA and Inflammatory Bowel Disease; and -all conditions in which endogenously produced IL-12 $\alpha/\beta$ or $\beta\beta$ forms are thought to play a disease-promoting role, including:
Pulmonary fibrosis
Pulmonary tuberculosis
Asthma
Sarcoidosis
Leprosy
Schistosomiasis
Lupus erythematosis
Lupus nephritis
Allograft rejection
Airway inflammation
Respiratory syncytial virus infection
Multiple sclerosis
Alzheimer's disease
Abortion (women with recurrent pregnancy loss)
Certain vaccines aimed at inducing TH2-type immune responses Experimental autoimmune myocarditis
Tuberculosis
Psoriatic arthritis
Rheumatoid arthritis
Osteoarthritis
Colonic inflammation (colitis)
Crohn's Disease
Inflammatory bowel disease
Atopic dermatitis, AD (chronic stage)
Inflammatory skin disease
Insulin dependent diabetes mellitus Type I and II
Endotoxaemia
Exposure to organic dust
Periodontal diseases
Nephrotic syndrome
Hepatocellular damage in chronic hepatitis C
Primary biliary cirrhosis
Cancer patients (Various cancers, and various stages in cancer that are typically accompanied with dysregulated IL-12, IL-23 and/or or IL-27 production)
ANCA associated vasculitis and sepsis
Experimental crescentic glomerulonephritis
Atherosclerosis
Acute viral myocarditis
Autoimmune myocarditis
Experimental autoimmune myastenia gravis
Uveitis (as Behret's disease)
Thyroiditis and Grave's disease
Thyroid autoimmune disease
Myelopathy (HTLV-1-associated myelopathy)
Symptomatic transient hypogammaglobulinaemia of infancy (THI)
Selective IgA deficiency. (SIgAD)
Schizophrenia
Primary malignant melanoma
Abdominal aortic aneurysm
Autoimmune thrombocytopenic purpura
Heatstroke
Meningococcal sepsis
Septic shock.
Meningoencephalitis
Bacterial meningitis
Pregnancy
Pre-eclampsia
HELLP syndrome (hemolysis, elevated liver function test and low platelet counts
Endometriosis
Acute pancreatitis
Lung fibrosis induced by silica particles
Scleroderma
Sjogren's syndrome
Ankylosis spondylitis
Hashimoto's thyroiditis
Autimmune anemias
Goodpasture's syndrome
Addinson's disease
Autoimmune hemolitic anemia
Spontaneous infertility (sperm)
Poststreptococcal glomerulonephritis
Autoimmune neuritis (Guillian-Barrd syndrome)
Sialadenitis
Brucellosis
Chickenpox and related viral diseases
*Helicobacter Pyloris*-induced gastritis
Common Variable Immunodeficiency (CVI)

In one embodiment, the disease is a conditions characterized by dysregulation of IL-12, IL-23 or IL-27 production conferred by polymorphisms in their respective genes, or by polymorphisms in genes involved in the biological activation or signal transduction pathway of these cytokines.

In one embodiment, the ER $Ca^{2+}$ perturbation reagent is selected from the compounds of Formula I:

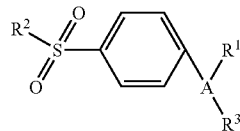

Formula I wherein A is a substituent selected from partially unsaturated or unsaturated hetrocyclyl and partially unsaturated or unsaturated carbocyclic rings;

wherein $R^1$ is at least one substituent selected from hetercyclyl, cycloalkyl, cycloalkenyl and aryl, wherein $R^1$ is optionally substituted at a substitutable position with one or more radicals selected from alkyl, haloalkyl, cyano, carboxyl, alkoxycarbonyl, hydroxyl, hydroxyalkyl, amino, alkylamino, arylamino, nitro, alkoxyalkyl, alkylsulfinyl, halo, alkoxy and alkylthio;

wherein $R^2$ is methyl or amino; and wherein $R^3$ is a radical selected from hydrido, halo, alkyl, alkenyl, oxo, cyano, carboxyl, cyanoalkyl, heterocycly-loxy, alkyloxy, alkylthio, alkylcarbonyl, cycloalkyl, aryl, haloalkyl, heterocyclyl, cycloalkenyl, aralkyl, hetrocyclylalkyl, acyl, alkythioalkyl, hydroxyalkyl, alkoxycarbonyl, arylcarbonyl, aralkylcarbonyl, aralkenyl, alkoxyalkyl, arylthioalky, aryloxyalkyl, aralkylthioalky, aralkoxyalkyl, alkoxyaralkoxyalkyl, alkoxycarbonalkyl, aminocarbonyl, aminocarbonylalkyl, alkyaminocarbonyl, N-arylaminocarbonyl, N-alkyl-N-arylaminocarbonyl, alkylaminocarbonylalkyl, carboxyalkyl, alkylamino, N-arylamino, N-aralkylamino, N-alkyl-N-aralkylamino, N-alkyl-N-arylamino, aminoalkly, alkylaminoalkyl, N-arylaminoalkyl, N-aralkylaminoalkyl, N-alkyl-N-aralkylaminoalky, N-alkyl-N-arylaminoalkyl, aryloxy, aralkoxy, arylthio, aralkylthio, alkylsulfinyl, alkylsulfonyl, aminosulfonyl, alkylaminosulfonyl, N-arylaminosulfonyl, arylsulfonyl, N-alkyl-N-arylaminosulfonyl; or a pharmaceutically-acceptable salt thereof.

In a preferred embodiment, the ER $Ca^{2+}$ perturbation reagent is selected from the compounds and compositions described in U.S. Pat. No. 5,972,986, Column 3, line 34 to Column 10, line 32. In a particularly preferred embodiment, the ER $Ca^{2+}$ perturbation reagent is a diaryl-substituted pyrazole marketed under the brand name CELEBREX (Celecoxib). CELEBREX is chemically designated as 4-[5-(4-methylpheny)-3-(trifluoromethyl)-IH-pyrazol-I-yl] benzenesulfonamide.

Alternatively, the ER $Ca^{2+}$ perturbation reagent may be thapsigargin or A23187.

The invention will be more clearly understood from the following description of some embodiments thereof, given by way of example only, with reference to the accompanying figures.

BRIEF DESCRIPTION OF THE FIGURES

FIG. 3. Primers used for amplification of the α and β chains of IL-12. (A) α chain forward primer (SEQ ID NO:1); (B) α-chain reverse primer (SEQ ID NO:2); (C) β chain forward primer (SEQ ID NO:3); (D) β-chain reverse primer (SEQ ID NO:4); and (E) β-chain reverse primer without histidine tag (SEQ ID NO:5). The sequence coding for the hexahistidine tag is represented in red, while initiation and stop codons are indicated in bold. The Kozak translation initiation sequence is underlined.

FIG. 4. Analysis of the amplification of the β-chain from LPS-induced U937 cells by means of 1.5% agarose gel electrophoresis. Lane 1, 100-bp DNA marker; Lane 2-4, β-chain fragment amplified in the presence of 2 mM $MgSO_4$ (lane 2); 3 mM $MgSO_4$ (lane 3) or 4 mM $MgSO_4$ (lane 4).

DETAILED DESCRIPTION OF THE INVENTION

Figure 1:
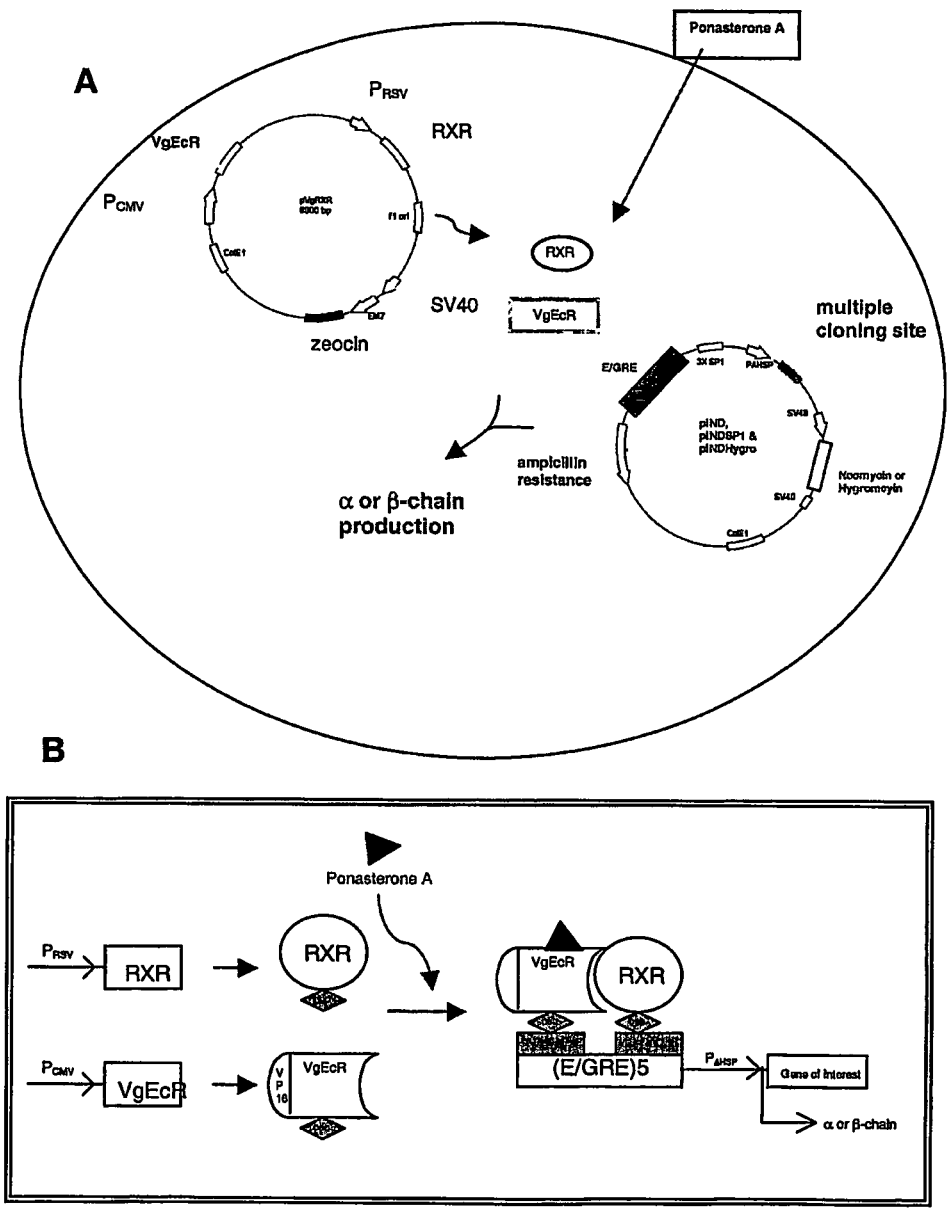
FIG. 1. is a schematic representation of the Ecdysone-Inducible Mammalian Expression System.

Recombinant cell lines that secrete various forms of IL-12 under control of tightly regulated promoters were generated. It was observed that treatment of these cell lines with an ER $Ca^{2+}$ perturbation reagent such as thapsigarin inhibited secretion of both the αβ and ββ forms of IL-12. The compound CELEBREX was also tested on assembly of IL-12, and found that it exerts a similar inhibitory effect on the secretion of the αβ and ββ forms of IL-12. There is a total block in the secretory production of both dimer forms of IL-12, and maximal effects are obtained with the normal physiological working concentration of CELEBREX in the absence of any apparent toxic effects as measured with the MTT assay. These affects are conferred in a post-transcriptional and post-translation manner as there is no effect on mRNA of IL-12. Without being bound by theory, evidence has been produced to support a $Ca^{2+}$-dependent disturbance in the folding pathway of IL-12 due to impaired activity of certain chaperones in the ER.

The inhibitory effect of CELEBREX on formation of the αβ and ββ forms of IL-12 in vitro indicates that this drug is of interest for the treatment of inflammatory conditions in which endogenous production of these IL-12 forms is known to lead to disease in a COX2-independent manner, including MS, IBD, virus-induced inflammation and asthma.

IL-12 is a member of a family of cytokines that includes two recently discovered members IL-23 and IL-27. All of these cytokines have a typical heterodimeric structure and display an array of both overlapping and distinct activities. It is thought that also IL-23 and IL-27 may contribute to destructive inflammation in various conditions. Most anticytokine drugs work by inhibiting transcription of mRNA. To our knowledge this is the first demonstration of a drug that inhibits cytokine formation in a post-translational manner on the level of folding and secretion of the protein, i.e. by perturbation.

Experimental Methods

Materials. Celecoxib (Celebrex) was obtained from Hefei Sceneri Chemical Co.; thapsigargin was obtained from Calbiochem and A23187 from Sigma.

Cell culture. HEK293 IL-12 β/β and α/β producing cell lines were maintained in a $CO_2$ incubator at 37° C. (5% $CO_2$). Cells were cultured in DMEM medium supplemented with 10% foetal bovine serum.

Cloning and Expression of the α and β Chain of IL-12
Extraction of mRNA from IL-12 Producer Cell Line Human monocytic U937 cells were kindly provided by the Rega Institute, Leuven, Belgium. U937 cells were grown in DMEM (Dulbecco's modified eagle medium) supplemented with 10% FBS, 2 mM L-glutamine (LifeTechnologies) and 50 µg/ml of gentamycin (Sigma). Cells were cultivated in 75 $cm^2$ flasks, in a $CO_2$ incubator (5% $CO_2$) at 37° C. and sub-cultured once a week by splitting 1/10 by means of trypsination with Trypsin-EDTA (LifeTechnologies) followed by centrifugation to remove trypsin. Cells were induced with IFN-γ (100 ng/ml) and LPS (1 µg/ml; Sigma) for 24 hours. Total RNA was extracted from cells ($10^7$) using StrataPrp® Total RNA Miniprep kit (Stratagene). This method uses a powerful denaturant, guanidine thiocyanate, in the lysis buffer. Afterwards, the sample was filtrated to reduce the amount of DNA and subjected to a silica-based fibre matrix to capture RNA.

Amplification of α and β-Chains of IL-12 by RT-PCR

To perform RT-PCR on the RNA extracted from IL-12 producer cells, we used the ProSTAR™ HF Single-Tube RT-PCR System (High FidelityY obtained from Stratagene. This method uses the StrataScript reverse transcriptase, which is subsequently inhibited by incubation at 95° C. Amplification is achieved with TaqPlus Precision polymerase. Oligonucleotides complementary to the sequences to be amplified (α and β-chain) were synthesized by LifeTechnologies. For the α-chain, the forward primer was designed to contain the second initiation methionine (ATG) and NheI restriction site (GCTAGC), while the reverse primer contained the stop codon (TAA), XhoI restriction site (CTCGAG) and a 6× Histidine tag sequence [3×(ATGGTG)]. The β-chain forward primer contained the initiation codon and the NheI restriction site as well. We synthesized two different oligonucleotides as reverse primers. The first one contains the stop codon, XhoI restriction site and the 6×His sequence, and the second was designed without the 6× Histidine sequence.

The RT-PCR reaction mix contained 5 µl of 10×HF RT-PCR buffer, 100 ng of forward primer; 100 ng of reverse primer, 200 µM of dNTP, 100 ng of RNA, 1 U of StrataScript RT (1 unit), and the Taqplus Precision DNA polymerase RT-PCR Conditions were:

| 42° C. | 30 min | 1 cycle |
|---|---|---|
| 95° C. | 1 min | 1 cycle |
| 95° C. | 30 sec | |
| 55° C. | 30 sec | 30 cycles |
| 68° C. | 2 min | |
| 68° C. | 10 min | 1 cycle |
| 4° C. | ∞ | |

The RT-PCR products were analyzed by means of 1.5% agarose gel electrophoresis coupled to staining in ethidium bromide for 30 minutes. The products were visualized on an UV transilluminator.

Amplification of the α and β-Chains of IL-12 Starting from the cDNAs

The cDNAs coding for the β-chain (p40) and α-chain (p35) of interleukin-12 were obtained from ATTC (American Type Tissue Culture Collection, N 40854) and HGMP Resource Centre (Human genome mapping project, Image Clone 1932948, www.hgmp.mrc.ac.uk), respectively. Pwo DNA polymerase from Boehringer Mannhein was the enzyme used for amplification. This enzyme has 3'-5' exonuclease proof-reading activity. Amplification was performed for 20 cycles (1 min at 95° C., 1 min at 47° C. and 1 min at 72° C.), using different concentrations of $MgSO_4$ (2, 3 and 4 mM), 200 µM dNTP (Pharmacia), 600 nM of each primer and 50 ng of template DNA. A Bio-Rad thermocycler was used for amplification of these products, and the primers used were the same as indicated above.

Purification of PCR Products

PCR products were purified by means of phenol/chloroform extraction. An identical volume of phenol/chloroform/isoamyl alcohol (25:24:1 v/v/v) was added to the samples. Samples were vortexed for 1 min and centrifuged at 18,000 rpm for 3 min, in order to separate the different phases. Subsequently, the aqueous phase was collected carefully. We removed the primers with cleaning columns from QIAGEN. As an alternative to the use of QIAGEN columns, ethanol precipitation was performed by adding 3 volumes of ethanol to the samples. 1/10 volume of sodium acetate (pH=5) was added to the reactions. Samples were left at −20° C. for 1 hour, and a DNA pellet was obtained by centrifugation at 18,000 rpm for 10 min at 4° C. Pellets were washed two times with 1 ml of 70% ethanol to remove salt and any organic molecules. The pellet was dried at room temperature and resuspended in 15 µl of TE buffer.

Restriction Digestion of the α and β-Chains

The PCR products were digested with the restriction enzymes NheI and XhoI which recognise the sequences

```
α-chain
Forward  5'CAGGCTAGCGCAGCCATGTGTCCAGCGCGCAGC3' (SEQ ID NO:1)
Reverse  5'CTGCTCGAGTTAATGGTGATGGTGATGGTGGGAAGCATT
         CAGATAGCT3' (SEQ ID NO:2)

β-chain
Forward  5'CAGGCTAGCGCAGCCATGTGTTCACCAGCAGTTG3' (SEQ ID NO:3)
Reverse  5'CTGCTCGAGCTAATGGTGATGGTGATGGTGACTGCAGGG
         CACAGATG3' (SEQ ID NO:4)
Reverse  5'CTGCTCGAGCTAACTGCAGGGCACAGATG3' (SEQ ID NO:5)
```

G↓CTAGC and C↓TCGAG, respectively. Both restriction endonucleases were supplied by Amersham Pharmacia.

One μl of each enzyme (8 and 9 units respectively) and 2 μl of 10×OPA⁺ (One-Phor-All Buffer Plus) buffer were added to 16 μl of purified PCR product, to make up a final volume of 20 μl. The reactions were incubated at 37° C. for 1.5 hours. The digestion was finalized by heat inactivation of the enzyme during 20 minutes at 65° C. followed by incubation at room temperature for 20 min. To concentrate the digestion products by precipitation, 1/10 volume of sodium acetate (pH=5) and ethanol were added to the reactions. Samples were left at −20° C. for 1 hour, and the pellet was obtained by centrifugation at 18,000 rpm for 10 min at 4° C. The pellet was washed 2 times with 1 ml of 70% ethanol. The pellet was allowed to dry at room temperature and resuspended in 15 μl of TE buffer.

The purified PCR products were subjected to 1.5% agarose gel electrophoresis in TBE buffer (45 mM Tris-Borate, 1 mM EDTA) and the bands (700 bp for α-chain and 900 bp for β-chain) were visualized after staining in TBE buffer supplemented with 0.5 μg/ml ethidium bromide (30 min) on a UV trans-illuminator.

Restriction Digestion of pIND, pIND(SP1) and pINDHygro Vectors

The pIND, pIND(SP1) and pINDHygro vectors (ecdysome-inducible mammalian expression vectors) were supplied by Invitrogen. These vectors each contain an ampicillin resistance gene for selection in *E. coli* cells, and either a neomycin (only pIND and pIND(SP1)) or an hygromycin resistance gene (pINDHygro) for selection in mammalian cells. 2 μg of each vector were digested with 8 units of NheI and 9 units of XhoI, in 1×OPA buffer in a final volume of 20 μl. Reactions were incubated at 37° C. for 1.5 hours and heat-inactivated at 65° C. for 20 min. The vector DNA was precipitated as described above.

Ligation of the α-Chain into pIND and pINDSP1, and of the β-Chain into pINDSP1 and pINDHygro Ligation of the digested PCR products (α and β-chains) into digested vectors was catalyzed by T₄ DNA ligase enzyme (Promega). Two different ratios of vector/insert (1:3 and 1:6) were tested in order to optimize the ligation reaction. The reactions were performed in a final volume of 20 μl, containing 2 μl of 10×T₄ ligase buffer, 1.5 units of T₄ DNA ligase, 3 μl of vector (100 ng), and the insert and vector DNA. The reactions were incubated overnight at 16° C.

Preparation of Competent Cells

*E. coli* JM109 (endA1, recA1, gyrA96, thi, hsdR17 (rₖ−, mₖ+), relA1, supE44, Δ(lac-proAB), [F', traD36, proAB, lacIᵠZΔM15] cells were made competent by means of the CaCl₂ method (REF). A single clone was inoculated in 5 ml of LB (Luria-Bertani broth containing 10 g/l bactotryptone, 5 g/l bacto-yeast extract and 10 g/l NaCl) medium and left overnight with vigorously shaking at 37° C. in a dedicated incubator. An aliquot of this culture (100 μl) was added to 5 ml of LB (Luria B) medium. This culture was further incubated at 37° C. until an OD (A₆₀₀) of 0.5 was reached (log phase). Cells were placed on ice for 5 minutes and then distributed (1 ml) in sterilized eppendorf tubes. These tubes were centrifuged at 13,000 rpm for 5 minutes, supernatants were discarded and pellets were resuspended in 1 ml of ice-cold CaCl₂. The cells were pelleted by centrifugation at 13,000 rpm for 5 minutes at 4° C., and washed in 1 ml of ice-cold CaCl₂; the pellet obtained was now resuspended in 200 μl of CaCl₂ and frozen at −70° C.

Transformation of *E. coli* Cells

Transformation was performed by mixing an aliquot of competent cells with the ligation reactions (7.5 μl). This mixture was incubated on ice for 1 hour and then subjected to a heat-shock at 42° C. for 2 minutes. 1 ml of LB medium was added, and this suspension was left at 37° C. for 1 hour with vigorously shaking. The transformation reactions were mixed with 0.7% agar supplemented with 50 μg/ml ampicillin and then plated on preheated (37° C.) LB 1.5% agar plates containing ampicillin (50 μg/ml). The plates were incubated overnight in an incubator at 37° C.

Plamid Purification from Transformed *E. coli* Cells

Colonies were inoculated in 5 ml of LB medium containing 50 μg/ml of ampicillin and left overnight with vigorously shaking at 37° C. in an incubator. Cells were collected by centrifugation at 6,000 rpm for 5 min. Pelleted cells were processed with the Qiagen miniprep purification kit. Qiagen plamid purification kits are based on an alkaline lysis procedure using a buffer composed of SDS, that disrupt the cell membranes, and NaOH, known to denature genomic DNA. The cell lysate is loaded onto an anion exchange resin that captures the DNA. Afterwards, RNA, proteins, dye and impurities are removed with a medium salt buffer (1 M NaCl). DNA is eluted by means of a buffer that contains 1.25 M NaCl. The eluted DNA is concentrated and precipitated with isopropanol.

Sequencing of pIND(SP1)-p35H, pIND-p35H, pIND-40H, pINDHygro-p40, pIND(SP1)-p40H and pIND-p40

The sequence of inserts was verified by the enzymatic dideoxy-method described by Sanger et al. (1977). The 'Ecdysone Forward' and 'BGH Reverse' primers were used for forward and reverse sequencing, respectively. The ABI PRISM Big DYE Terminator Cycle Sequencing Ready Reaction Kit was used. A mixture was prepared consisting of 8 μl of the Terminator Ready Reaction Mix, 3.2 pmol of each primer and 500 ng of DNA, and deionized water was added to a volume of 20 μl. PCR conditions were 25 cycles 15 sec at 50° C., 25 cycles

| | |
|---|---|
| 60° C. | for 4 min |
| 4° C. | ∞ |

Prior to sequencing, PCR products were purified in order to remove dNTPs, primers and unincorporated dye terminators. Ethanol precipitation was carried out by adding 2 μl of 3 M sodium acetate pH=4.6, and 50 μl of 95% ethanol to the PCR products. Samples were vortexed and left at room temperature for 15 minutes. Subsequently, the samples were centrifuged at 18,000 rpm (4° C.) for 20 minutes. The supernatant fractions were discarded and the pellet was washed two times with 270 μl of 70% ethanol. The pellet was dried at room temperature, followed by resuspension in 5 μl deionized formamide and 25 mM EDTA to which blue dextran was added (50 mg/ml). The samples were heated at 95° C. for 2 minutes before being loaded on an ABI PRISM 310 Genetic Analyzer.

Cell Cultivation and Transfection

Maintenance of Cells

The human embryonic kidney cell line (EcR-293), previously transfected with a pVgRXR construct that encodes the regulatory ecdysone receptor, was obtained from Invitrogen. The cells were cultured in DMEM (LifeTechnologies) supplemented with 10% of foetal bovine serum (LifeTechnologies) and L-glutamine 2 mM, in addition to 400 μg/ml zeocin, 400 μg/ml hygromycin or 600 μg/ml G418 for selection of transfected cells (Invitrogen). Cells were cultivated in 75 cm² flasks until 80% of confluency was reached. Medium was removed and trypsin-EDTA solution was added. After 15 minutes at 37 C, medium was added and cells were collected. The suspensions were centrifuged at 1,000 rpm for 5 min. in order to remove the trypsin. Cells were resuspended in medium and transferred to new culture flasks. Cells were generally split 1 over 10 once a week. Cells were maintained in a $CO_2$ incubator at 37° C. (5% $CO_2$).

Freezing of EcR-293 Clones Expressing IL-12 α or β-Chains

Selected clones were cultivated in 175 $cm^2$-flasks until they reached 80% confluency. The cells were collected by trypsinization, and counted in a hemacytometer by means of the trypan blue exclusion assay—REF). Cells were resuspended at a density of $3 \times 10^6$ cells/ml in the freezing medium, which was composed of 90% medium and 10% DMSO, and these suspensions were transferred to cryovials. The cryovials (LifeTechnologies) were placed at –20° C. for 2 hours, transferred to a –70° C. freezer for 16 hours and, finally, placed in liquid nitrogen for long-term storage.

Transfection of Mammalian Cells

Plasmid DNA used for transfection of mammalian cells was purified by means of the Endofree kit of QIAGEN. The purified plasmid DNA was quantified by spectrophotometry. DNA concentrations were determined by measuring absorbance at 260 nm, and the purity was estimated by the $A_{260}/A_{280}$ ratio.

EcR293 cells were plated in 6-well plates ($2 \times 10^5$) the day before the transfection. Transfections of EcR293 cells were performed by means of the FuGENE-6 transfection reagent (Boehringer Mannheim). FuGENE-6 is a cationic lipid reagent which interacts with negatively charged DNA to form a complex that can cross the cell membrane. We used 1 or 2 μg of plasmid DNA (pIND(SP1)-p35H, pINDHygro-p40 or pIND-p40H) to transfect cells. DNA samples were mixed with 3 μl of FuGENE-6, and diluted in 97 μl of medium. This solution was directly added to the cells.

Preparation of Soluble and Insoluble Fraction of Cells

Monolayers of EcR293 cells were washed 3 times with large volumes of PBS. Cells were scraped and resuspended in PBS, and centrifuged. The pelleted cells were resuspended in lysis buffer, and incubated on ice for 30 minutes. Lysis buffer was composed of PBS, supplemented with 5 mM EDTA, 5 mM EGTA, 1×protease inhibitors (Boehringer Mannheim), and 1% Triton X-100. Subsequently, the samples were centrifuged at 18,000 rpm for 10 minutes, and the soluble fraction recovered. The insoluble fraction was washed with PBS supplemented with 1% Triton X-100, and centrifuged at 18,000 rpm for 10 minutes. Both the soluble and insoluble fractions were now ready for analysis by SDS-PAGE and immunoblot.

Gel Electrophoresis (SDS-PAGE)

Sodium dodecyl sulphate polyacrylamide electrophoresis (SDS-PAGE; Laemmli, 1970) was used as a standard technique for separating proteins in the culture medium, soluble/insoluble cell fractions, and immunoprecipitates. Generally, protein samples were mixed with 2×SDS-PAGE loading solution and loaded into the wells of pre-cast 4-15% polyacrylamide gels. Electrophoresis was performed at high voltage (200V) using a BioRad Mini-Protean III electrophoresis unit and a Pharmacia power supply. The electrophoresis buffer used contained 25 mM Tris, 192 mM glycine, and 0.1% SDS (pH=8.3). Size standards, such as the 'Perfect Protein Western Blot Marker' from Novagen, were included in every gel.

Western Blotting, Antibodies and Detection

Immunoblot

Following SDS-PAGE, proteins were transferred from the gel to a PVDF membrane by semi-dry electroblotting. The polyacrylamide gel and 2 stacks of pre-cut Whatman filter papers were equilibrated in transfer buffer (48 mM Tris, 39 mM glycine, 0.04% SDS, 20% methanol) for 10 minutes. A PVDF membrane was briefly soaked in methanol. The gel and the PVDF membrane were placed between two stacks of ten layers of filter papers, and the whole was transferred to an electro-blotting unit. The electrotransfer conditions applied were 0.8 mA/$cm^2$ for 1 hour. The apparatus was dismantled, and the membrane was incubated overnight at 4° C. in blocking buffer (2% casein in TBS consisting of 10 mM Tris-HCl, pH=7.4, and 100 mM NaCl). The membrane was incubated with a primary antibody. We used the following antibodies: (i) mouse α-p35 antibody G161-566, obtained from BD-PharMingen, and used at a working concentration amounting to 1/10,000 of the original stock; (ii) mouse α-p40 antibody C8.6, BD-PharMingen, used at a 1/5,000 dilution; or (iii) the mouse anti-IL-12 antibody 1-2A1 obtained from Abcam, 1/1, 000 diluted. For detection of chaperones we used the following antibodies: (i) anti calreticulin, and (ii) anti-GR894, from Stratogen.

These primary antibodies were added to TBS-T, i.e. TBS supplemented with 0.5% Tween-20 and 0.1% casein. Incubation was done at room temperature for 2 hrs. Membranes were washed repeatedly with TBS-T buffer (without casein), and subsequently incubated with a secondary antibody. The secondary antibody used was either goat anti-mouse or goat anti-rabbit horseradish-peroxidase-conjugated antibody from Jackson&ImmunoResearch (used at a 1/20,000 dilution). Incubation was performed for 1 hour at room temperature, after which membranes were washed again. The 'Perfect Protein Western Blot Marker' was detected by means of an S-protein HRP conjugate (Novagen), used at a working concentration of 1/5,000 of the orginal stock. Detection of polyhistidine tagged fusion proteins was carried out using the INDIA™ His Probe-HRP purchased from Pierce. In this case, following overnight blocking, the membrane was incubated with INDIA HisProbe (1/5,000 dilution) in TBS-T buffer with 0.1% casein.

Chemiluminiscent Detection

Chemiluminiscent detection was carried out with either the 'ECL' or 'ECL+Plus' kit, both purchased from Amersham-Pharmacia. The ECL detection principle is based on the oxidation of luminol (cyclic diacylhydracide), while ECL+Plus uses the enzymatic generation of an acridinium ester. The latter produces a more intense light emission of longer duration. According to the manufacturer, the ECL kit can generally detect 1 pg of antigen, while the ECL+Plus kit can detect 20 times less protein. When using the ECL kit, the working solution was prepared by mixing equal parts of the 'Luminol/Enhancer' and 'Peroxidase' solutions. When using the ECL+Plus kit, the working solution was prepared by mixing 40 parts of the 'Substrate' solution with 1 part of 'Acridan' solution. The membrane was incubated with these solutions for 5 or 1 minute(s), respectively. Excess solution was removed from the membrane. The membrane was wrapped in cling film, and exposed using Kodak MR1 or MR2 films.

Stripping and Reprobing of Membranes

Primary and secondary antibodies were removed from the membranes by incubation in stripping buffer (100 mM 2-mercaptoethanol, 2% SDS, and 62.5 mM Tris-HCl; pH=6.7). Incubation was allowed to proceed for 30 min. to 1 hour at 50-60° C. The membrane was washed in TBS-T for 1 hour and blocked in 2% casein. At this stage, the membrane was ready for re-incubation with a primary antibody.

Purification of the Recombinant α and β Subunits of IL-12
$Ni^{2+}$-NTA Chromatography Purification of hexahistidine-tagged α- and β-chains was performed using nickel-nitrilotriacetic acid ($Ni^{2+}$-NTA) affinity chromatography. $Ni^{2+}$-NTA agarose was obtained from QIAGEN.

Cross-Linking of Proteins

Following induction, cells were washed, scraped and resuspended in PBS supplemented with 100 μg/ml of dithiobis(succinimidylpropionate) (DSP). DSP is a homobifunctional NHS-ester that reacts with the ε-amines of lysines residues, so as to form a covalent amide bond. Cross-linking reactions were incubated at room temperature for 30 minutes, with intermittent vortexing performed every 5 minutes. Reactions were quenched by adding 100 mM of Tris.HCl (pH=8.0). As Tris contains DSP-reactive primary amines, the aim of this 'quenching' reaction is to block any remaining unreacted DSP. Quenching was allowed to proceed for 15 minutes.

Inhibitor and Cytotoxicity Assays

Inhibitor Assay

To analyse the effect of inhibitors on formation and secretion of IL-12, generally cells were grown in 12-well plates. When the cells reached a confluency of 70%, inhibitors were added to the culture medium at the concentrations indicated. After 2 hours of incubation, cells were induced with ponasterone A. Sixteen to twenty-four hrs later, medium was collected to analyse secretion of α and β-chains, either alone or in combination. Cells were lysed as described above, and soluble and insoluble fractions were prepared. In some experiments, the α- and/or β-chains were purified by means of Ni2+-NTA agarose affinity chromatography.

| | INHIBITION OF | Concentration |
|---|---|---|
| A23187 | Ionophore | 0.1 to 30 μM |
| CELEBREX | Cox-2 Inhibitor | 10 to 100 μM |
| Thapsigargin | ER Ca-ATPase | 5 μM |

Cytotoxicity Test

The mitochondrial ...MTT test is widely use as a cytotoxicity test. This test is principally based on the propensity of mitochondrial dehydrogenases to cleave the tetrazolium ring of. The viability of cells is proportional to the activity of mitochondrial dehydrogenases. Cleavage of the tetrazolium ring results in the formation of purple formazan crystals. We used the MTT assay to quantify cytotoxicity of celecoxib on EcR293 cells. The test was performed in 96-well plates in which $10^5$ cells per well were plated the day before application of the MTT test. Following addition of celecoxib to the culture medium, cells were induced by ponasterone A, as explained before. After 16 hours of induction, the MTT reagent (10 μl of 100 mg/ml stock solution) was added to the cells. Two hours later, the medium was removed, and the cells were dissolved in DMSO. DMSO solubilizes formazan crystals. Absorbance was measured at 550 nm using a 96-well plate spectrophotometer.

Description of the Ecdysone-Inducible Mammalian Expression System

As a means to study folding and secretion of dimeric forms of interleukin, a series of cell lines that produce the recombinant. α and β-chain under transcriptional control of a chemically inducible promotor were developed. The expression system used is based on the ability of the insect hormone ecdysone (analog Ponasterone A) to induce transcription of IL-12 in mammalian cells from a compatible promoter. Since mammalian cells do not express the ecdysone receptor, the basal levels of transcription of IL-12 were low or non-existent. The hormone ecdysone (or its analogs) does not affect the physiology of mammalian cells, and hence, can be used without inducing any other irrelevant or toxic effects. This expression system facilitates extremely tight control of the expression of α and β-chain genes, which is of interest for both kinetic studies and studies in which inhibitors are used as a means to monitor the process of folding and secretion of IL-12.

Architecture and Components of the Ecdysone-Inducible Mammalian Expression System The Ecdysone-Inducible Mammalian Expression System (EIMES) is based on the use of a heterodimer composed of the ecdysone receptor (VgEcR) and the retinoid X receptor (RxR)(FIG. 1A). Both receptors are coded for in the cell line by the plasmid pVgRxR vector that carries the zeocin resistance gene, allowing for selection by means of this antibiotic. The ecdysone receptor is under transcriptional control of the Rous sarcoma virus promoter ($P_{RSV}$) while the retinoid receptor is located downstream from the cytomegalovirus promoter ($P_{CMV}$). Both are constitutive promoters facilitating continuous production of high levels of the heterodimer. The ecdysone receptor contains the VP16 transactivation domain which increases the level of induction. In the presence of ponasterone A (ecdysone analog) the ecdysone and retinoid X receptors will bind to each other, and the heterodimerized receptor will subsequently bind to the ecdysone/glucocorticoid response element (E/GRE) sequence present in the promoter of pIND vectors to be used as vehicle for expression of IL-12 chains (FIG. 1B). Both receptors have a DNA binding domain (DBD) which recognises half of the response element (E/GRE). The DBD of the ecdysone receptor recognises 5'AGTGCA3' and the DBD of the retinoid receptor recognises the sequence 5' AGAACA3' (Yao et al., 1993). The response element is upstream from the promoter that activates gene expression ($P_{ΔHSP}$) in pIND. Thus the binding of the receptor heterodimer to these response elements will induce the transcription of the gene of interest (FIG. 1B). The cell line used is EcR293, a derivative of the HEK293 cell line that is transfected with the pVgRXR vector and cultivated in the presence of zeocin.

pIND Expression Vectors for Production of IL-12

Figure 2:
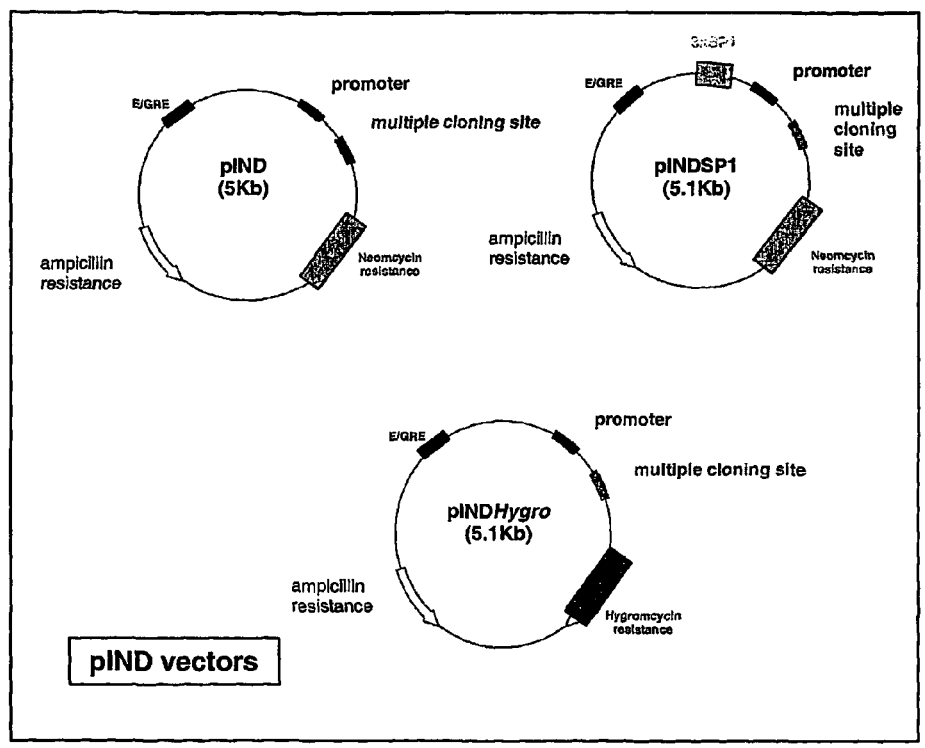
FIG. 2. is a schematic overview of the pIND, pINDSP1 and pINDHygro vectors.

Three different pIND vectors (pIND, pINDSP1 and pINDHygro) are available all of which can be used in this expression system to produce recombinant proteins (FIG. 2). All of these contain an ampicillin resistance gene to enable selection and propagation of clones in E. Coli cells. The multiple cloning site is located downstream from a minimal heat shock promoter ($P_{\Box HSP}$). pIND and pINDSP1 differ from pINDHygro in that the first two vectors contain the neomycin resistance gene while pINDHygro contains the hygromycin resistance gene. These different antibiotic resistance genes allow for dual selection of transfected cells in the presence of both antibiotics. This is important in view of the requirement of producing cell lines that express both subunits of dimeric interleukins, with each subunit provided by a different vector.

The pINDSP1 vector contains three SP1 binding sites inserted between the response elements and the promoter, which theoretically increases the expression levels five times in comparison with pIND (Kadonaga et al., 1987).

Rational for use of Histidine Tags

The use of the histidine tag as a means for purification of recombinant proteins is a well-documented method proven to be highly efficient. The major advantages of this system are: Purification can be achieved from a mix containing less than 1% of total protein in one-step. Purification can be completed under native or denaturing conditions since the binding of the histidines to the Ni-NTA agarose is not dependent on the conformation. The His tag is a small tag and it does not interfere with the structure or function of the protein to be expressed so removal of the tag is not necessary. The His tag can be used as the target to be recognized by an antibody anti-His tag. The histidine tag can be engineered so as to be expressed in the target protein in either N- (preceded by ATG initiation codon) or C-terminal (followed by TAA, TGA or TAG stop codon) position. This is accomplished through the use of specific primers which are designed so as to contain the coding sequence for 6 histidines fused to the sequence of our target protein. By means of metal ionic affinity chromatography (matrix used $Ni^{2+}$-nitrilotriacetic acid coupled to agarose, abbreviated as Ni-NTA) His-tagged recombinant proteins can be captured and purified in a highly selective and specific manner. This strategy was applied to the purification of the IL-α and β-chains from both cell lysates (in order to capture protein in the process of folding in the endoplasmic reticulum and to co-capture proteins associated with the folding chains such as chaperones) and medium (so as to capture fully folded and matured secreted protein).

Amplification of α and β Chains of IL-12

Design of Primers

The composition of the nucleotide sequence preceding the ATG translation initiation codon is known to affect translation initiation. Therefore primers optimized for translation were designed (consensus sequence: GCCRCC ATG). To clone both subunits directionally into the multiple cloning sites of pIND plasmids, an NheI restriction site was introduced in the forward primers and an XhoI restriction site in the reverse primers (FIG. 3). The α and β-chain sequences of IL-12 (Sequence ID No.s 6 and 7) (Genbank accession numbers: M65291 and M65290) were checked to assure that none of these contain these restriction sites.

The IL-12 α-chain sequence contains two initiation codons (ATG), which occur in the same reading frame and are 99 nucleotides apart. It has been demonstrated that α-chains translated from either the first or second start codon are functional. Thus, the initiation codon used may affect the length of the signal peptide, but does not affect primary structure and folding of the mature chain. This is understandable since folding occurs in the ER after the signal peptide has been removed. The forward primer was designed to contain the second start codon of the functional α-chain. The reverse primer contained the stop codon (TAA) and the sequence for six histidines engineered between the carboxy-terminus and the stop codon. Similarly, the β-chain primers contained ATG and TAG stop codons. For the β chain, however, two reverse primers were designed, i.e. one containing the sequence coding for the six histidines and the other without the histidine tag (FIG. 3).

Amplification of the α and β Chains of IL-12 by RT-PCR from U937-Extracted mRNA

In order to obtain mRNA of the IL-12 α and β chains, a monocytic cell line (U937) was induced with LPS for 16 hours, a treatment which is known to result in the production of IL-12 in this cell line. The RNA was extracted, and mRNA was retrotranscribed into cDNA by RT-PCR using the primers described in the preceding paragraph and the high-fidelity thermostable Pwo DNA polymerase. Since the concentration of $MgSO_4$ is known to influence the specificity of primer annealing three different concentrations of $MgSO_4$ were used in the PCR reaction. Subsequently, the amplification products were analysed by means of 1.5% agarose gel electrophoresis. Though a band was visible that corresponded to the expected length of the amplified β chain (900 bp; FIG. 4), no amplification product was obtained for the α chain (not shown).

Amplification of the α and β Chains of IL-12 by PCR from cDNA

Figure 5:
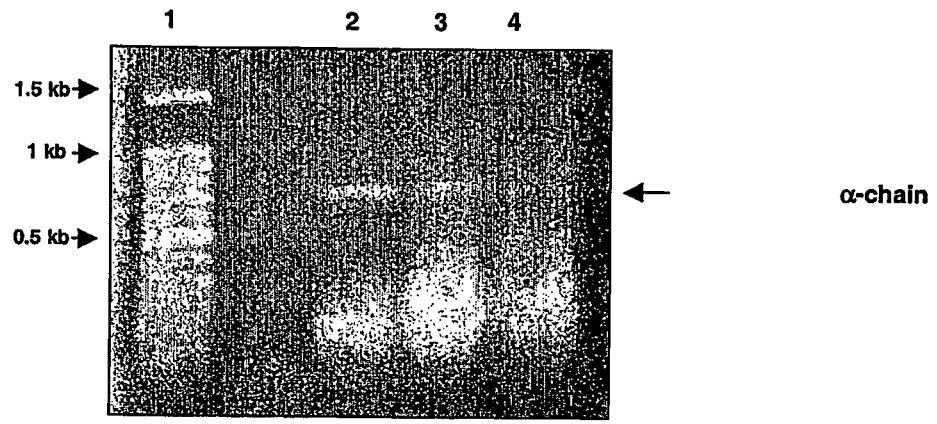
FIG. 5. Amplification of α-chain cDNA (702 bp). Lane 1, 100-bp DNA marker; Lane 2-4, α-chain fragment amplified in the presence of Pwo DNA polymerase and 2 mM $MgSO_4$ (lane 2); 3 mM $MgSO_4$ (lane 3) or 4 mM $MgSO_4$ (lane 4).
Figure 6:
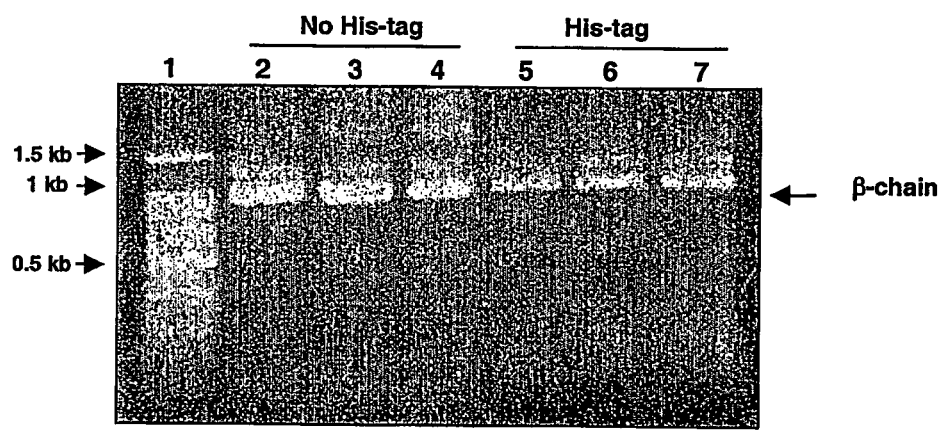
FIG. 6. Amplification of β-chain cDNA (1029 bp). Lane 1, 100-bp DNA marker; Lane 2-4, β-chain fragment amplified in the presence Pwo DNA polymerase of 2 mM $MgSO_4$ (lane 2); 3 mM $MgSO_4$ (lane 3) or 4 mM $MgSO_4$ (lane 4). Lanes 1-3 correspond to products obtained using the reverse primer without the histidine tag and lanes 5-6 including the histidine tag.

The α and β-chains were amplified using as template the full-length cDNAs obtained from the ATCC and the HGMP Resource Centre, respectively. Again, we decided to use Pwo DNA polymerase for amplification rather than Taq polymerase, since the former displays 3'→5' exonuclease proofreading activity which is known to reduce the accumulation of errors in the final PCR product. The reactions were carried out as explained in section 2.1.3. The PCR products obtained by amplification of the cDNAs of the α and β-chains were analyzed by means of 1.5% agarose gel electrophoresis. FIG. 5 illustrates the amplification of the α-chain: a PCR product corresponding to 700 bp was specifically amplified in the presence of 2-3 mM $MgSO_4$. FIG. 6 shows the 900-bp PCR product obtained following amplification of the cDNA of the β-chain.

Construction of pIND-Derived Expression Vectors

Introduction

Figure 7:
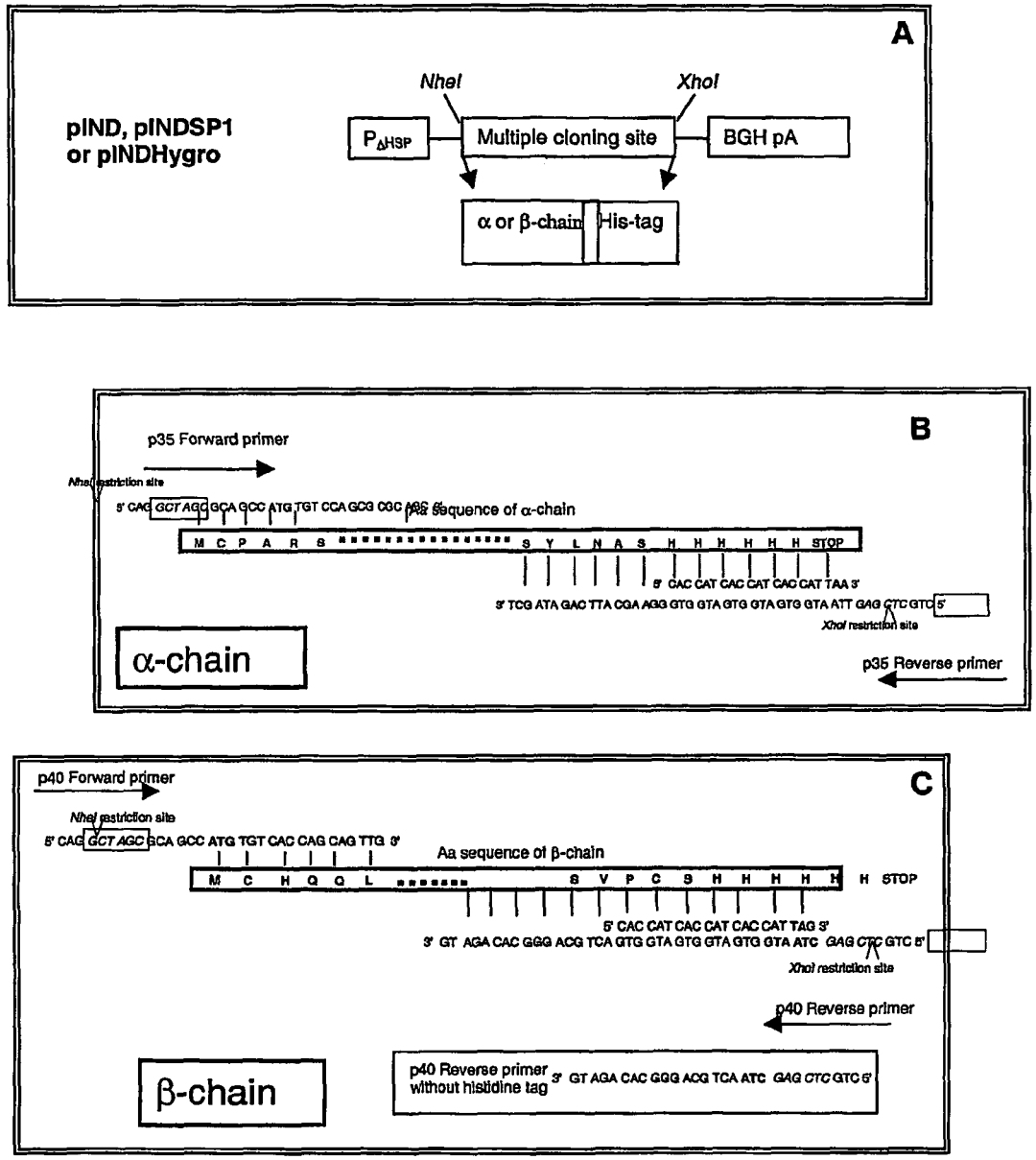
FIG. 7. Expression cassettes for the α and β-chains of IL-12 in the series of pIND vectors. (A) Expression cassette shared by all vectors of the pIND series with indication of the location of the minimal heat shock promoter ($P_{\Delta HSP}$) and the bovine growth hormone poly-adenylation signal (BGH pA); (B) and (C) 5' and 3' nucleotide sequences and corresponding amino- and carboxy-terminal amino acid sequences of the recombinant α (B) and β (C) chains with indication of the primer sequences. The α chain forward primer (SEQ ID NO:1) and reverse primer (SEQ ID NO:2) are shown in (B). The β-chain forward primer (SEQ ID NO:3) and reverse primer (SEQ ID NO:4) are shown in (C). The β-chain reverse primer without histidine-tag (SEQ ID NO:5) is also shown in (C).

The PCR products were purified and digested with NheI and XhoI, and subsequently cloned into NheI/XhoI-cut vectors. 5 different constructs were created, i.e. pIND-p35H, pIND(SP1)-p35H, pINDHygro-p40, pIND(SP1)-p40H and pIND-p40. The expression cassettes for the α and β chains of IL-12 contained within these vectors are specified in FIG. 7. As explained above, pIND(SP1) and pINDHygro confer resistance to different antibiotics, i.e. neomycin and hygromycin respectively, when expressed in mammalian cells. Thus, expression vectors were constructed that would facilitate selection of the following stable cell lines:

1. EcR293 cells expressing the carboxyterminal-Histagged α-chain selected by the antibiotic neomycin (transfected with either pIND-p35H or pIND(SP1)-p35H, anticipated to differ only in the level of expression);
2. EcR293 cells expressing the β-chain selected with neomycin (pIND-p40 or pIND(SP1)-p40H, differing in level of expression but also in the presence or absence of a carboxyterminal His-tag);
3. EcR293 cells expressing the β-chain selected with hygromycin (pINDHygro-p40)
4. EcR293 cells expressing the α/β heterodimer selected with both neomycin and hygromycin (pINDHygro-p40 and either pIND-p35H or pIND(SP1)-p35H).

Selection and Sequencing of Clones

Competent *E. coli* JM109 cells were transformed with these different constructs. Following transformation, the cells were plated on Petri dishes containing LB-agar supplemented with ampicillin. pIND vectors confer resistance to ampicillin to *E. coli* cells that have successfully integrated the plasmid. However, still the presence or absence of an insert in the vector has to be verified. In order to confirm the presence of the insert three complementary methods were adopted. First, colony PCR was performed facilitating the identification of positive clones by means of direct amplification of the insert using α and β-chain-specific primers. Second, the presence of the insert by NheI/XhoI restriction digestion of plasmid minipreps and electrophoresis. Third, forward and reverse sequencing was performed to validate the presence of the insert and the absence of any errors. The results of the colony PCR procedure are illustrated in FIGS. 8 and 9, which show that not every ampicillin-resistant colony appeared to contain the insert.

Figure 8:
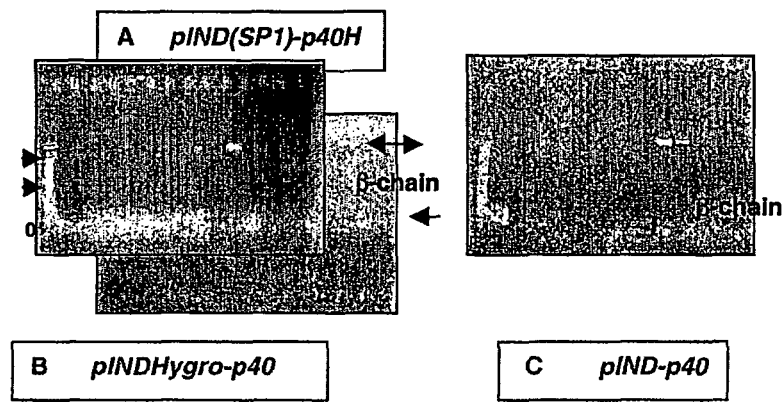
FIG. 8. Electrophoresis of amplification products obtained by colony PCR of ampicillin-resistant clones. The photographs show the results obtained from clones transformed with (A) pIND(SP1)-p40H; (B) pINDHygro-p40; and (C) pIND-p40.
Figure 9:
FIG. 9. Electrophoresis of amplification products obtained by colony PCR of ampicillin-resistant clones following transformation with pIND(SP1)-p35H FIG. 10. Confirmation of the presence of inserts by means of restriction analysis of minipreps. (M) 100-bp ladder; (A) pIND(SP1)-p35H digested with NheI and XhoI (insert of 700 bp); (B) pINDHygro-p40 digested with NheI and XhoI; and (C) pIND(SP1)-p40H digested with NheI and XhoI (inserts of 900 bp). Note: the vector portions were too large to penetrate into this high-percentage agarose gel and are therefore not visible.
Figure 10:
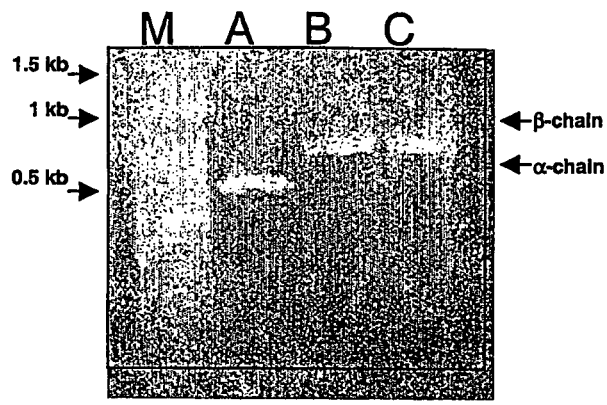

The positive colonies that were identified in FIGS. 8 and 9 were propagated in LB medium supplemented with ampicillin, and minipreps and glycerol stocks were prepared. To confirm the presence of the insert in the plasmid minipreps were digested with NheI and XhoI restriction enzymes and these products were subjected to 1.5% agarose gel electrophoresis (FIG. 10).

The third method utilised to verify that the plasmids extracted from ampicillin-resistant clones contained the correct inserts corresponding to either α and β-chains, consisted of dideoxynucleotide DNA sequencing. Forward and reverse sequencing was performed using the multiple cloning site primers, i.e. ecdysone forward primer and BGH reverse primer. This showed that error-free inserts were present in the right orientation in each of the vectors.

Development of Stably Transfected EcR293 Cell Lines

Extraction of Endotoxin-Free Plasmid DNA to be Used for Transfection of EcR293 Cells The plasmids were purified using the Endofree purification kit from QIAGEN. This kit facilitates large-scale extraction of plasmid DNA from 100 ml of bacterial cultures while efficiently removing endotoxins. Endotoxins are toxic for mammalian cells, and their presence in DNA preparations may decrease transfection efficiency. The DNA of the purified samples was quantified by spectrophotometry ($A_{260}$). The concentrations obtained ranged between 0.4 and 2 µg/µl (Table 1). The purity of DNA samples was calculated by absorption measurements at 260 and 280. A ratio A260/280 amounting to 1.8 to 2 is indicative for a very high purity. As can be seen in Table 1, both the amounts and purities of the plasmid DNA obtained using the Endofree kit were highly satisfactory.

Table 1. Concentration, total amount and purity of plasmid DNA extracted from bacterial cultures with the Endofree kit

| Plasmid | $A_{260}$ | Conc. | Total Amt. | Ratio (Purity) |
|---|---|---|---|---|
| pIND(SP1)-p35H | 0.051 | 0.577 µg/µl | 115.4 µg | 1.825 |
| pIND Hygro-p40 | 0.070 | 2.059 µg/µl | 411.5 µg | 1.876 |
| pIND-35H | 0.097 | 0.998 µg/µl | 199.6 µg | 1.809 |
| pIND-p40 | 0.047 | 0.478 µg/µl | 95.6 µg | 2.082 |
| pIND(SP1)-p40H | 0.098 | 1.07 µg/µl | 214 µg | 1.89 |

Transfection and Selection of EcR293 Cells

EcR293 cells were transfected with these vectors, either alone or in combinations. Following 1 day of recovery after transfection, cells were trypsinized, diluted and seeded into 96-well plates. The appropriate antibiotics were added to the culture medium to initiate the selection process. As summarized in Table 2, three different cell concentrations and two different antibiotic concentrations were used to perform selection over time.

Vectors and vector combinations used to transfect EcR293 cells:

| | | |
|---|---|---|
| 1-pIND-p35H | 3pIND-p40 | 6-pIND-p35H/pINDHygro-40 |
| 2-pIND-(SP1)-p35H | 4pINDHygro-p40 | 7-pIND(SP1)-35H/ |
| | 5pIND(SP1)-p40H | pINDHygro-p40 |

TABLE 2

Cell and antibiotic concentrations for selection of transfected EcR293 cells

| | | Conc. Neomycin | Conc. Hygromycin | Conc. Zeocin |
|---|---|---|---|---|
| $10^6$ transfected cells | Dilution 1/10 ($10^5$ cells/well) | 300 µg/ml | 300 µg/ml | 400 µg/ml |
| | | 600 µg/ml | 600 µg/ml | 400 µg/ml |
| | Dilution 1/100 ($10^4$ cells/well) | 300 µg/ml | 300 µg/ml | 400 µg/ml |
| | | 600 µg/ml | 600 µg/ml | 400 µg/ml |
| | Dilution 1/1000 ($10^3$ cells/well) | 300 µg/ml | 300 µg/ml | 400 µg/ml |
| | | 600 µg/ml | 600 µg/ml | 400 µg/ml |

For the construct made with the pINDHygro vector (pINDHygro-p40), selection was performed in the presence of either 300 or 600 µg/ml hygromycin. These concentrations were chosen on the basis of the concentrations of hygromycin recommended by the manufacturer of the pIND series of vectors for selection of transfected EcR293 cells (between 200 and 600 µg/ml). Similarly, cells transfected with pIND- and pINDSP1-derived vectors were cultivated in the presence of either 300 or 600 µg/ml neomycin, as recommended. Hygromycin concentration of 200 µg/ml was used in all further transfection experiments with pINDHygro-p40. After 6 weeks we were able to detect about 40 different clones in total, generated by transfection with the different constructs and selection with the appropriate antibiotics.

Figure 11:
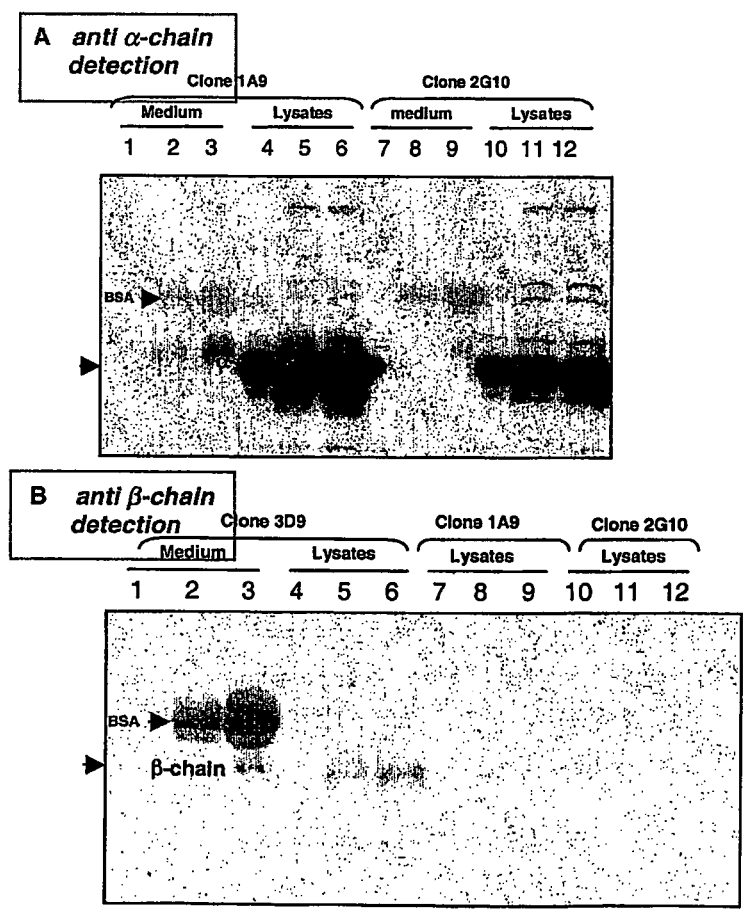
FIG. 11. Analysis of ponasterone A-inducible expression of IL-12 α (A) and β (B) chains in transfected cell lines. 4-15% reducing SDS-PAGE analysis of clones 1A9 (His-tagged α-chain), 2G10 (His-tagged α-chain) and 3D9 (β-chain). (A) detection with monoclonal anti-p35 antibody. 1 (lane 1), 5 (lane 2) and 10 (lane 3) μl of the medium, and 1 (lane 4), 5 (lane 5) and 10 μl (lane 6) of the soluble cell lysate of ponasterone A-induced clone 1A9 were submitted to 4-15% SDS-PAGE and immunoblotted. Lanes 7-12 represent similar fractions of clone 2G10. (B) detection with monoclonal anti-p40 antibody. Lanes 1-6: fractions of medium and cell lysate of clone 3D9 as described for (A); Lanes 7-12: cell lysates of clones 1A9 and 2G10, used as negative control.

Immunodetection of Expression of α and β Chains Following Induction with Ponasterone A As a test in order to evaluate whether these clones were able to produce the corresponding recombinant proteins, we selected three clones, i.e. 1 single clone for pIND-p35H (clone 1A9), 1 for pIND(SP1)-p35H (clone 2G10) and 1 for pIND-p40 (clone 3D9). These clones were trypsinized and plated into the wells of 6-well plates. The cells were induced with Ponasterone A (5 µM) for 48 hours. Subsequently, the cell culture medium was collected, and the cells were lysed. This was done to evaluate the presence of the recombinant protein in both secreted and intracellular fractions. Culture medium and soluble cytoplasmic fractions were subjected to 4-15% reducing SDS-PAGE (FIG. 11). The proteins were transferred by electroblot to a PVDF membrane. Immunodetection was performed with anti-IL-12 α- or β-chain antibodies. Immunoreactive bands were visualized using a chemoluminiscence-based kit and autoradiography films, Kodak BioMax MR films. (ECL kit; see sections 2.7).

Figure 12:
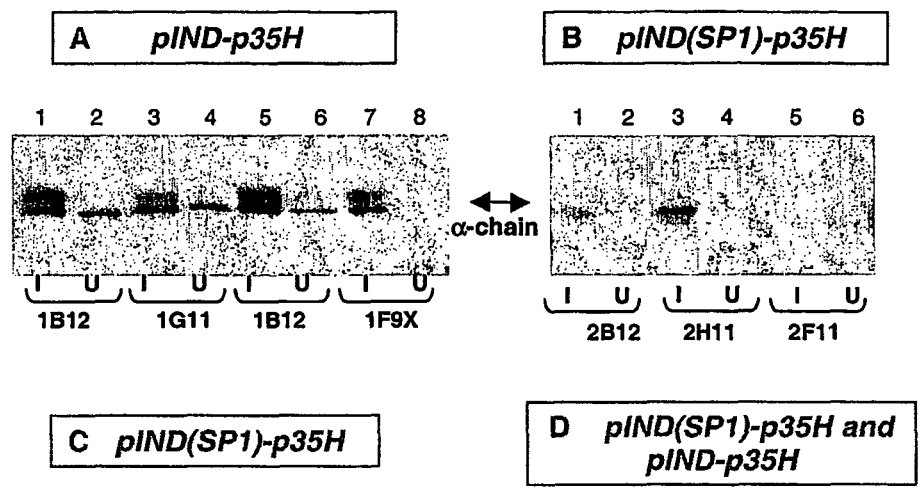
FIG. 12. Expression levels of the IL-12 α chain in 18 different neomycin-resistant EcR293 clones. Anti-α-chain immunoblots of soluble cell lysates were prepared from induced (I) and uninduced (U) EcR293 clones obtained following transfection and neomycin selection with (A) pIND-p35H; (B, C) pIND(SP1)-p35H and (D) pIND-p35H or pIND(SP1)-p35H. Lysates were subjected to reducing SDS-PAGE using 4-15% gels, blotted and immunodetected with anti α-chain antibody. As negative control, we used the secreted fraction of clone 4B6Z, which expresses the β-chain (lane 13-14 in FIG. 16D).
Figure 13:
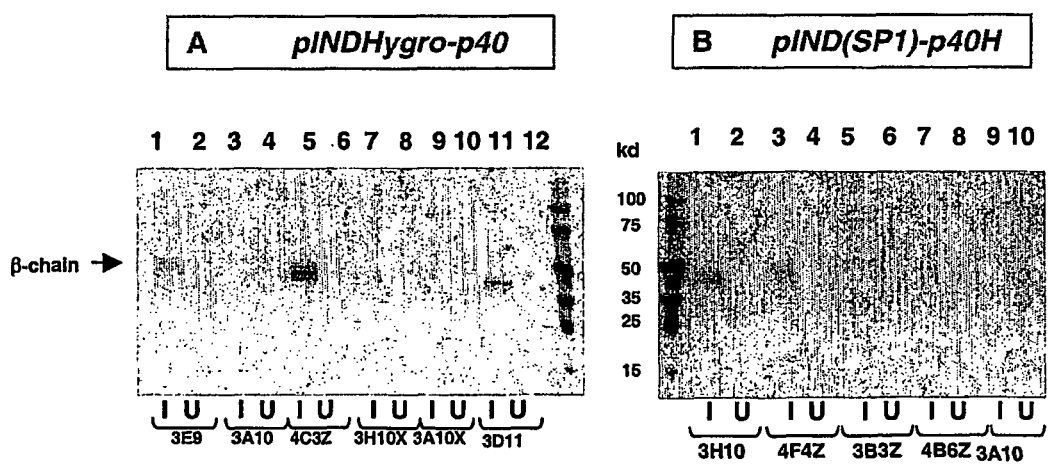
FIG. 13. Expression levels of the IL-12 β chain in hygromycin-(A) and neomycin-(B) resistant EcR293 clones. Anti-α-chain immunoblots of soluble cell lysates prepared from induced (I) and uninduced (U) EcR293 cells. Clones were obtained by transfection with (A) pINDHygro-p40; or (B) pIND(SP1)-p40H. Lysates were subjected to SDS-PAGE using 4-15% gels, blotted and immunodetected with anti α-chain antibody.

This first analysis indicated that p40 is more efficiently secreted than p35, as the ratio of secreted/intracellular is obviously higher for the former. Finally, a band corresponding to the Mr of serum albumin was visible in all immunoblots of medium fractions (indicated with arrow in FIG. 11 A and B). A similar immunoreactive band was found in the medium of uninduced or untransfected cells, indicating that this band is unrelated to any of the IL-12 chains but is likely visualized following a—specific interaction with either the primary or secondary antibodies used in these experiments (not shown).
Differences in Expression Levels in Stably Transfected Cell Lines Having demonstrated the inducible expression of immunoreactive proteins corresponding to either the α or the β chain of IL-12 in some of the EcR293 cell clones produced, the expression levels in all of the clones were evaluated by means of a similar procedure. For this purpose cells, precedingly seeded in 96 well plates ($5 \times 10^4$ cells) were induced with ponasterone A for 24 hours. Induced and uninduced cells were lysed in 6 µl of lysis buffer, and the lysates were subjected to 4-15% reducing SDS-PAGE and immunoblot (FIGS. 12 and 13).

Surprisingly, an anti-α-chain reactive band was observed in the lysates of both un-induced and induced EcR293 cells that exhibited a slightly lower Mr than the inducible, recombinant α-chain. This band was also consistently observed in immunoblots of un-transfected EcR293 cells (not shown). Thus, this protein is likely to correspond to a natural, constitutively produced form of either p35 or a p35-related protein in these cells. Its Mr is smaller than that of the recombinant form, which is likely due to the absence of the hexahistidine-tag in the natural form. Nevertheless, the smaller form is unlikely to correspond to a proteolytically generated truncated form of the recombinant his-tagged α-chain as it is equally present in un-induced or un-transfected cells.

Most of the cell lines were freezed and kept in liquid nitrogen. Cell line 2B9 (FIG. 12, lane 1-2), which appeared to be the cell line with the highest expression level of the α-chain was maintained in cultivation for further experiments. This cell line was re-named HACHIE.1. Similarly, cell line 3H10 which expresses high levels of the β-chain (FIG. 13B, lane 1-2) was maintained in culture. This cell line was re-named HIBERNIA.1.

Transient Transfection of HIBERNIA.1 Cells to Produce Heterodimeric IL-12

As described above, HIBERNIA.1 is a cell line that produces high levels of carboxyterminally hexahistidine-tagged β-chain upon induction with ponasterone A, and was obtained by transfection of EcR293 cells with pIND(SP1)-p40H followed by selection with neomycin. The transient transfection was carried out in 6-well plates using 1 or 2 µg of endotoxin-free pIND(SP1)-p35H plasmid DNA. Cell culture medium was collected at 30 and 48 hours following induction. The samples were run in a non-reducing gel so as to facilitate detection of the disulfide-bonded heterodimer. Following electrophoresis, semi-dry blotting was performed, and the membrane was successively probed with an anti-β-chain (FIG. 14) and an anti-α-chain antibody (FIG. 14).

Figure 14:
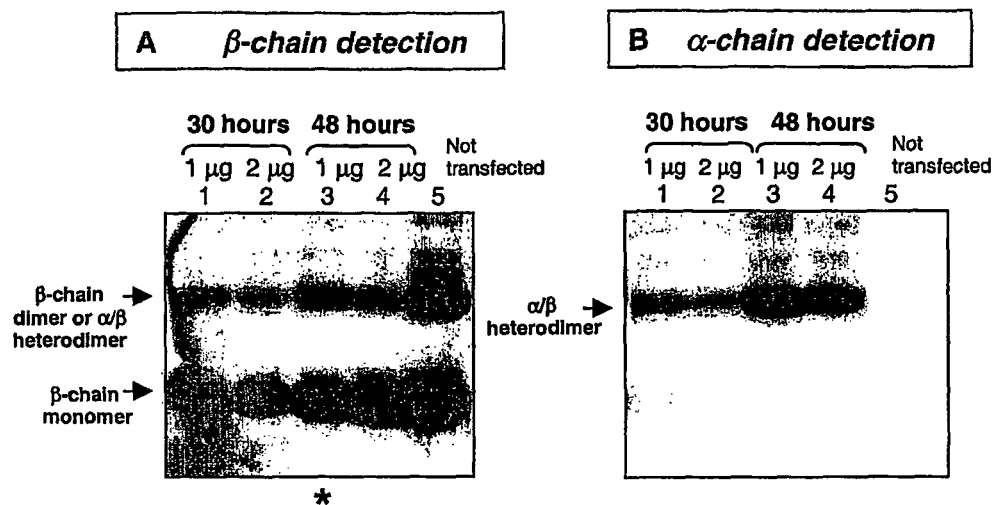
FIG. 14. Transient transfection of HIBERNIA.1 cells with pIND(SP1)-p35H. Non-reducing 4-15% SDS-PAGE and immunoblot of secreted fractions of the transfected cell line following 30 (lanes 1 and 2) and 48 (lanes 3 and 4) hrs of induction with ponasterone A. The cells were transfected with 1 (lanes 1 and 3) or 2 (lanes 2 and 4) □g of pIND(SP1)-p35H. As a control the secreted fraction of the non-transfected induced β-chain-producing HIBERNIA.1 cells was used (lane 5). (A) detection with anti β-chain antibody; (B), detection with anti α-chain antibody.

FIG. 14 shows that in the culture medium of both the transiently transfected (lanes 1 to 4) and not-transfected (lane 5) HIBERNIA.1 cells 2 immuno-reactive bands are detected with the anti-β-chain antibody, with Mr's of about 40 and 80 kD respectively. In lanes 1 to 4, the 80-kD band could represent the β chain homodimer (2×40 kD) as well as the α/β chain heterodimer (35+40 kD), as both would migrate as bands with similar Mr in this low-resolution SDS-PA gel. In not-transfected HIBERNIA.1 cells (lane 5 of FIG. 14) the 80 kD band must necessarily represent the β chain homodimer. FIG. 14 shows that a 80-kD protein band which is reactive with the anti-α-chain antibody is present only in HIBERNIA.1 cells transfected with pIND(SP1)-p35H (lanes 1 to 4) but not in un-transfected HIBERNIA.1 cells (lane 5). Analysis of recombinant cell lines secreting the a chain by means of non-reducing SDS-PAGE showed that the a chain is present only as a monomer form when expressed in the absence of the β chain (data not shown). In view of these findings, it can be safely concluded that HIBERNIA.1 cells transiently transfected with pIND(SP1)-p35H secrete the α/β disulfide-bonded IL-12 heterodimer upon induction with ponasterone A. In fact, in these cells the total amount of α chain secreted ends up as subunit of the heterodimer form, as anti-α-chain reactivity is only visible as an 80-kD band and not as a 35-kD band. However, it is likely that a certain fraction of the β chain produced in transiently transfected HIBERNIA.1 cells will still be present as homodimer. This possibility is difficult to exclude in view of the fact that the non-transfected HIBERNIA.1 cells produce the β homodimer.

Transfection of HIBERNIA.1 cells with with 1 µg pIND(SP1)-p35H resulted in a higher production/secretion of the heterodimer compared to transfection with 2 µg. This might be related to the fact that due to the 1:1 stoichiometry of α and β chain interaction in the heterodimer, a level of α-chain production which is higher than that of the β chain may be counterproductive for efficient formation of the heterodimer.

To verify the composition of the 80-kD band secreted by transiently transfected HIBERNIA.1 cells, we run the medium collected at 48 hrs after induction from HIBERNIA.1 cells transfected with 1 µg of pIND(SP1)—p35H (* in FIG. 14), again, this time in a reducing gel. Gels were blotted, and detection was carried out with either the anti-1-chain antibody, the anti-β-chain antibody or with both antibodies at the same time.

Figure 15:
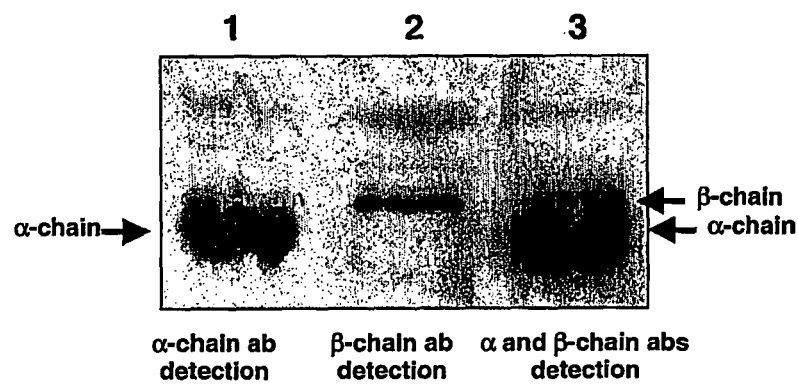
FIG. 15. Immunodetection of α and β subunits of IL-12 in medium of HIBERNIA.1 cells transiently transfected with pIND(SP1)-p35H following reducing SDS-PAGE. Lane 1, detection with anti α-chain antibody; Lane 2, detection with anti-β-chain antibody, Lane 3, detection with both antibodies at the same time.
Figure 16:
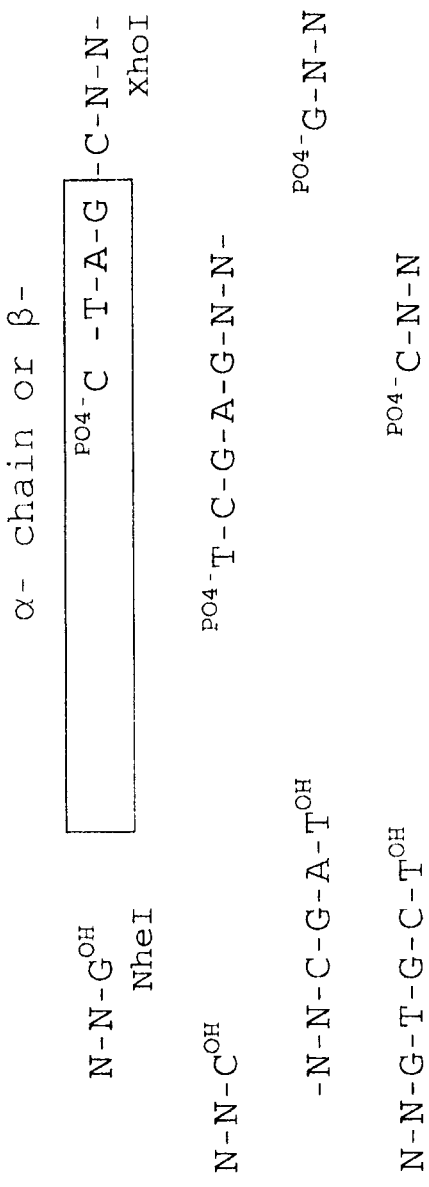
Fig. 16. Digestion of α-chain or β-chain with restriction enzymes NheI and XhoI.

The anti-α-chain antibody detected a band corresponding to 35 kD, while the anti-β-chain antibody detected a band of approximately 40 kD (FIG. 15). Thus, the Mr's of the α and β chains produced in transiently transfected HIBERNIA.1 cells coincide with those theoretically predicted. The α chain appeared as a more diffuse band than the β chain. This is most likely due to more extensive heterogeneity in N-glycosylation of the former, as tunicamycin treatment produced a much sharper α-chain band (demonstrated below).

This data shows that a genuinely processed α-chain form is produced in transiently transfected HIBERNIA.1 cells that interacts with the β-chain to form a disulfide-linked secreted IL-12 heterodimer. Obviously, these experiments show that attachment of hexahistidine-tags to the carboxytermini of both the α- and β-chains does not interfere with correct folding, assembly and secretion of the heterodimer.

Capture of α/β- and β/βIL-12-H6-Chaperone Complexes on $Ni^{2+}$-NTA

Following induction with Ponasterone A, cells were lysed. -α/β and β/β-$H_6$-chaperone complexes were captured on $Ni^{2+}$-NTA agarose. The gel was washed 5 times with buffer A (100 mM NaH2PO4, 10 mM Tris HCl, 8M urea, pH 6.3), and elution was carried out with buffer B (same as Buffer A, but pH 4.3). Complexes were boiled in SDS loading solution+DTT. Proteins were separated by 4-15% SDS-PAGE and transferred to PVDF membranes. Detection was carried out using anti-p35 antibody G161-566.14 (Pharmingen). Membranes were stripped and re-probed successively with anti-chaperone antibodies (α-CRT, α-Grp78, α-Grp94 & α-CNX; StressGen).

Experimental Findings

IL-12 is a secretory protein. Secretory proteins are defined as proteins that are released by cells into the extracellular milieu, and that exert their biological activity by binding onto a specific membrane receptor of target cells. 'Folding' (i.e. generation of a correct three-dimensional structure) of secretory proteins, such as IL-12, typically occurs in a membrane-surrounded cell organelle, named the endoplasmic reticulum (ER). The ER is specifically enriched in chaperones, thioredoxin-type isomerases and proteins involved in glycosylation pathways. An important role of these factors is to assist in ensuring correct folding of secretory proteins during their transit in the ER prior to their secretion into the extracellular milieu. Improperly folded secretory proteins are generally retained in the ER and subsequently degraded by proteases and components of the cytosolic proteasome. It was hypothesised that the use of selected pharmacological agents that interfere with the proper functioning of 'folding'-assisting factors in the ER could be used to inhibit proper folding, and, hence, secretion of IL-12. As a first step, different tightly controlled ecdysone-inducible recombinant cell lines expressing functional C-terminally hexahistidine-tagged IL-12 α/β (heterodimer) and IL-12 β/β (homodimer) chains were developed. The use of such recombinant cell lines alleviates some of the problems related to the use of natural producer cells of IL-12 (e.g. restricted availability, lack of reproducibility etc). These recombinant cell lines were used as a means to study the processes that determine regulation of folding, assembly and secretion of IL-12 homo- and heterodimers. The following inhibitors were used: (i) thapsigargin (an ER $Ca^{2+}$-ATPase inhibitor), and (ii) the ionophore A23187 and (iii) celecoxib (a putative ER $Ca^{2+}$ perturbating reagent), each over a wide range of concentrations.

Following a 16-hr treatment of cells with these inhibitors, culture medium was collected and the presence of secreted IL-12 forms was detected by means of non-reducing SDS-PAGE and western immunoblot. It was found that neither the α/β nor the β/β dimer forms of IL-12 were present in the culture medium of cells treated with thapsigargin when this was added over a concentration range of 0.1 μM to 15 μM. The amount of extracellularly secreted IL-12 dimer forms produced by thapsigargin-treated cells was <5% of that produced by untreated cells (maximal suppression was observed for all concentrations of thapsigargin greater than or equal to 0.1 μM). Similarly, the calcium ionophore A23187 suppressed formaton of secreted IL-12 dimer forms when it was used over a concentration range of 0.1 μM to 30 μM, with maximal suppression (>95% compared to untreated cells) from 1 μM. Toxicity conferred by these inhibitors over the test period of 16 hr as measured with the MTT test was observed for concentrations of thapsigargin >5-10 μM and for concentrations of A23187 >10 μM. Thus, the maximal suppression of secreted IL-12 dimer production is achieved at an inhibitor concentration at which toxic effects are totally absent, showing that both IL-12-suppressive and cell-toxic effects conferred by these inhibitors are independent. Secretion of IL-12 α and β monomer forms was suppressed by neither thapsigargin nor A23187.

Both thapsigargin and A23187 are likely to exert these effects by decreasing the concentration of $Ca^{2+}$ in the ER. It is likely that the resulting suboptimal concentration of $Ca^{2+}$ in the ER blocks the activity of $Ca^{2+}$-dependent chaperones and folding-assisting proteins involved in the dimer formation of IL-12. It was investigated whether CELECOXIB can be used to suppress production of secreted IL-12 dimer forms.

Celecoxib was dissolved in DMSO and added to recombinant HEK293 cells over a concentration range from 10 μM to 100 μM. As a control DMSO-only treated cells were used. Celecoxib concentrations were chosen on the basis of available literature data, and coincide with optimal activity of the compound in various cell-based systems. Two hours later cells were induced with Ponasterone A to produce IL-12 α/β or β/β dimer forms. After 16 hrs of additional incubation, culture medium was collected and assessed for the presence of IL-12 dimer forms by means of non-reducing SDS-PAGE and immunoblot. This showed that Celecoxib suppressed production of secreted IL-12 β/β homodimers by >95% when used at a concentration equal to or larger than 30 μM; and of secreted IL-12 α/β heterodimers by >95% when used at a concentration equal to or larger than 10 μM. Secretion of IL-12 α and β monomer forms was not suppressed by Celecoxib. Toxicity as measured with the MTT assay was visible when cells were treated for 16 hrs with a concentration of Celecoxib equal to or larger than 100 μM.

The present data demonstrates that Celecoxib efficiently suppresses secretion of IL-12 α/β and β/β dimer forms by a post-transcriptional and post-translational mechanism that involves $Ca^{2+}$-dependent intracellular retention of IL-12 dimers. Maximal IL-12-suppressive effects are observed at a physiological Celecoxib concentration in the absence of any obvious toxic effects.

For oral administration, the medicament according to the invention may be in the form of, for example, a tablet, capsule suspension or liquid. The medicament is preferably made in the form of a dosage unit containing a particular amount of the active ingredient. Examples of such dosage units are capsules, tablets, powders, granules or a suspension, with conventional additives such as lactose, mannitol, corn starch or potatoes starch; with binders such as crystalline cellulose, cellulose derivatives, acacia, corn starch or gelatins; with disintegrators such as corn starch, potaote starch or sodium carboxymethyl-cellulose; and with lubricants such as talc or magnesium stearate. The active ingredient may also be administered by injection as a composition wherein, for example, saline, dextrose or water may be used as a suitable carrier.

For intravenous, intramuscular, subcutaneous, or intraperitioneal administration, the compound may be combined with a sterile aqueous solution which is preferably isotonic with the blood of the recipient. Such formulations may be prepared by dissolving solid active ingredient in water containing physiologically compatible substances such as sodium chloride, glycine, and the like, and having a buffered pH compatible with physiological conditions to produce an aqueous solution, and rendering said solution sterile. The formulations may be present in unit or multi-dose containers such as seated ampoules or vials.

If the inflammatory disease is localized in the G.I. tract, the compound may be formulated with acid-stable, base-liable coatings known in the art which began to dissolve in the high pH intestine.

Formulations to enhance local pharmacologic effects and reduce systemic uptake are preferred.

Formulations suitable for administration conveniently comprise a sterile aqueous preparation of the active compound which is preferably made isotonic. Preparations for injections may also be formulated by suspending or emulsifying the compounds in non-aqueous solvent, such as vegetable oil, synthetic aliphatic acid glycerides, esters of higher aliphatic acids or propylene glycol.

Formulations for topical use include known gels, creams, oils, and the like. For aerosol delivery, the compounds may be formulated with known aerosol exipients, such as saline and administered using commercially available nebulizers. Formulation in a fatty acid source may be used to enhance biocompatibility. Aerosol delivery is the preferred method of delivery for epithelial airway inflammation.

For rectal administration, the active ingredient may be formulated into suppositories using bases which are solid at room temperature and melt and dissolve at body temperature.

Commonly used bases include cocoa butter, glycerinated gelatin, hydrogenated vegetable oil, polyethylene glycols of various molecular weights, and fatty esters of polyethylene stearate.

The dosage form and amount can be readily established by reference to known inflammatory disease treatment or prophylactic regiments. The amount of therapeutically active compound that is administered and the dosage regimen for treating a disease condition with the compounds and/or compositions of this invention depends on a variety of factors, including the age, weight, sex and medical condition of the subject, the severity of the disease, the route and frequency of administration, and the particular compound employed, the location of the inflammatory disease, as well as the pharmacokinetic properties of the individual treated, and thus may vary widely. The dosage will generally be lower if the compounds are administered locally rather than systemically, and for prevention rather than for treatment. Such treatments may be administered as often as necessary and for the period of time judged necessary by the treating physician. One of skill in the art will appreciate that the dosage regime or therapeutically effective amount of the inhibitor to be administered may need to be optimized for each individual. The pharmaceutical compositions may contain active ingredient in the range of about 0.1 to 2000 mg, preferably in the range of about 0.5 to 500 mg and most preferably between about 1 and 200 mg. A daily dose of about 0.01 to 100 mg/kg body weight, preferably between about 0.1 and about 50 mg/kg body weight, may be appropriate. The daily dose can be administered in one to four doses per day.

Although the data presented is based predominantly on the provision of cell lines that when induced produce either homodimeric or heterodimeric IL-12, or either subunit of IL-12, the invention is also applicable in the production of cell lines which when induced produce either IL-23 and IL-27, or subunits thereof. In the case of IL-23, a suitable host cell, such as one which includes an ecdysone-inducible mammalian expression system as described herein, is transformed with a first expression vector according to the invention which includes DNA coding for the p40 (beta) subunit of IL-12 (which is identical to the p40 subunit of IL-23) and a second expression vector which includes DNA coding for the p19 subunit of IL-23. In this regard, the cDNA sequence of the p19 subunit of IL-23 is provided in Sequence ID No. 8. The cDNA is processed by the same restriction enzymes as used with the respective subunits of IL-12, and is ligated into, for example, a pIND vector is the same manner as is described above. Likewise, expression vectors having DNA coding for one of the subunits of Il-27, and cell lines transfected with such expression vectors, may be produced using the techniques described herein.

The invention is not limited to the embodiments hereinbefore described which may be varied in detail without departing from the invention.

The invention claimed is:

1. A method of screening a candidate compound for the ability to inhibit dimer assembly and secretion of a dimeric form of interleukin, comprising the steps of:

incubating a cell culture comprising a cell line transfected with an expression vector comprising DNA encoding a subunit of a dimeric form of interleukin under transcriptional control of an ecdysone-inducible promoter with the candidate compound, wherein the subunit is selected from the group consisting of p35 (alpha) subunit of IL-12; p40 (beta) subunit of IL-12; p19 subunit of IL-23; p40 subunit of IL-23; ebi3 subunit of IL-27; and p28 subunit of IL-27;

inducing transcription of dimeric interleukin in the cells of the culture by contacting the cells with ecdysone or an ecdysone analog; and assaying the cell culture for the presence of secreted dimeric interleukin.

2. The method as claimed in claim 1, in which the dimeric interleukin expressed by the cell line has a 6× histidine amino acid sequence tagged on either or both of the subunits thereof, wherein the assaying step comprises Ni-NTA affinity chromatography.

3. The method as claimed in claim 1 in which the assaying step comprises probing the cell culture with an antibody specific to a dimeric form of interleukin, or a subunit thereof.

4. The method according to claim 1 wherein the cell line is capable of producing heterodimeric IL-12, the cell line being transfected with an expression vector in which the DNA encodes p40 (beta) subunit of IL-12 and an expression vector in which the DNA encodes p35 (alpha) subunit of IL-12.

5. The method according to claim 1 wherein the cell line is capable of producing heterodimeric IL-23, the cell line being transfected with an expression vector in which the DNA encodes p40 (beta) subunit of IL-12 and an expression vector in which the DNA encodes p19 subunit of IL-23.

6. The method according to claim 1 wherein the cell line includes plasmid pVgRxR.

7. The method as claimed in claim 1 in which the cell line comprises cells which are human embryonic kidney cells.

8. The method according to claim 1 in which the cell line comprises human embryonic kidney cells which include plasmid pVgRxR.

9. The method according claim 1 in which the cell line comprises cells which are natural β subunit-producing cells.

10. The method according to claim 1 in which the cell line is the cell line having ECACC accession number 03112701.

* * * * *